(12) United States Patent
Sharpe et al.

(10) Patent No.: US 8,603,396 B2
(45) Date of Patent: Dec. 10, 2013

(54) CELL ANALYSIS APPARATUS AND METHODS

(75) Inventors: Johnathan Sharpe, Hamilton (NZ); Kenneth Michael Evans, College Station, TX (US)

(73) Assignee: XY, LLC, Navasota, TX (US)

( * ) Notice: Subject to any disclaimer, the term of this patent is extended or adjusted under 35 U.S.C. 154(b) by 238 days.

(21) Appl. No.: 13/058,574

(22) PCT Filed: Aug. 21, 2008

(86) PCT No.: PCT/US2008/073915
§ 371 (c)(1),
(2), (4) Date: Feb. 11, 2011

(87) PCT Pub. No.: WO2010/021627
PCT Pub. Date: Feb. 25, 2010

(65) Prior Publication Data
US 2011/0143389 A1    Jun. 16, 2011

(51) Int. Cl.
*G01N 15/06* (2006.01)
*G01N 33/00* (2006.01)
*G01N 33/48* (2006.01)

(52) U.S. Cl.
USPC ............. 422/68.1; 422/50; 422/81; 436/43

(58) Field of Classification Search
USPC ................ 422/50, 68.1, 81; 436/43
See application file for complete search history.

(56) References Cited

U.S. PATENT DOCUMENTS

| 2006/0177937 A1* | 8/2006 | Kurabayashi et al. ......... 436/63 |
| 2008/0221812 A1* | 9/2008 | Pittaro et al. .................... 702/66 |
| 2009/0006003 A1* | 1/2009 | Hirayama et al. .............. 702/21 |
| 2009/0268195 A1* | 10/2009 | Ilkov ............................. 356/73 |

* cited by examiner

*Primary Examiner* — Brian J Sines
(74) *Attorney, Agent, or Firm* — Ryan Christensen; Cindee R. Ewell

(57) ABSTRACT

Particular embodiments of the inventive technology relate to 'off-axis detector' technology that employs a third detector 23 exhibiting a flow orthogonal axis 43 as defined by its EMR collection angle, where such axis is from 30 degrees to 60 degrees from an intended, flow orthogonal, cell cross section long axis alignment line 13, in addition to employing a fourth detector 24 exhibiting a flow orthogonal axis 44 as defined by its collection angle, where such axis is orthogonal to the flow orthogonal, third detector axis 43. Particular embodiments of the inventive technology relate to 'axially spaced illumination' technology featuring more than one cell illumination site, where, other than the most upflow illumination site (e.g., 121), all illumination site(s) are downflow of at least one other illumination site. Particular embodiments of the inventive technology may feature aspects of both technologies.

23 Claims, 26 Drawing Sheets

A

B

C

D

A

B

C

A  B

CELL ANALYSIS APPARATUS AND METHODS

This application is the United States National Stage of Patent Cooperation Treaty International Patent Application No. PCT/US2008/073915, filed Aug. 21, 2008 which is hereby incorporated by reference herein.

TECHNICAL FIELD

Embodiments of the inventive technology relate generally to particle analysis. More particularly, certain embodiments of the inventive technology relate to the analysis of aspherical cells using flow cytometers and microfluidic-based apparatus and, possibly, sorting of such aspherical cells (e.g., sperm cells).

BACKGROUND ART

Cell analysis apparatus, including flow cytometers and microfluidic analysers, are conventionally used to analyze and, at times, sort cells. Whether in order to sort X-chromosome sperm cells from Y-chromosome sperm cells, or to accomplish some other particle analysis (e.g., cell analysis), flow cytometers in particular, have an established reputation as an effective, albeit imperfect, analysis apparatus. Apparatus featuring microfluidic technologies, while representing a promising approach to the difficult problem of rapid particle analysis, have a less established reputation and are currently the subject of much attention and innovative design effort; accordingly, they are not used commercially to the extent the "tried-and-true" flow cytometers are.

Nonetheless, as mentioned, those using flow cytometers would welcome improvements, especially those that increase the proportion of cells whose analysis results are reliable. For example, the analysis results of 25% to 40% of sperm cells that the conventionally best flow cytometers analyze are unreliable; such cells typically go to waste. Of course, particularly in applications where the analyzed sperm cells are particularly valuable (sperm from a prize bull, an endangered species, as but two examples) such waste is highly undesirable. Further, such waste comes with wasted apparatus use time, and may discourage owners of, e.g., prize bulls, from selling their bull semen for sorting. Such problems, in general, are not unique to sperm sorting applications; indeed, any application that seeks to properly analyze (i.e., so as to produce reliable results) aspherical cells may find that conventional flow cytometers result in 25% to 40% of wasted cells.

The specific problem with flow cytometers, and perhaps certain microfluidic apparatus, stems from the difficulty in fully orienting (in plane that is orthogonal to the flow) cells, as many flow cytometer designs, in order to properly analyze aspherical cells (including but not limited to sperm cells) require not only that a cell be oriented relative to a flow axis (such that the cell long axis is parallel to the flow axis, which is relatively easy to do to all, if not 98+% of cells passing through the channel), but also that the cell be properly radially oriented, such that the long axis of the flow orthogonal, cell cross section (typically a non-circular cross-section) is aligned with an intended, flow orthogonal, cell cross section long axis alignment line that is defined by the channel. The reason for the need for such radial orientation has to do with the fact that the most reliable electromagnetic (EMR) detector readings (e.g., readings of EMR intensity emitted as a result of the cell illumination): (1) are of EMR (electromagnetic radiation) emitted out a lateral side (as opposed to the edge) of the cell/cell portion; and (2) result when the cell is illuminated upon projection of EMR on a lateral side. Such reliable readings can then be compared to yield accurate conclusions about an intrinsic characteristic of the cell (e.g., whether a sperm cell bears an X or Y chromosome).

In order to achieve such reliable readings, certain known flow cytometer designs employ a radially orienting channel (including a radially orienting nozzle tip and/or a beveled injection needle, as examples) designed to radially orient a cell such that a fixed EMR projector projects EMR at a lateral side of the cell (e.g. the lateral side of a flow orthogonal cross section of a sperm cell's head) and EMR emitted from a lateral side of the cell as a result of such illumination (e.g., as a result of fluorescence by stained DNA that are illuminated) can be read by a fixed detector. However, in order to determine whether a cell is in a fully radially oriented position, a different EMR detector is positioned to detect EMR emitted from the edge of the fully oriented cell (e.g., an edge of a flow orthogonal cross section of a sperm cell's head); readings from this "intended" "edge-on" detector are compared with the readings of the "intended" "side-on" detector. If indeed the reading from the intended "edge-on" detector (which may be said to provide information relative to said cell orientation) relates to the reading of the intended "side-on" detector in a manner that is found during a full radial orientation (for example, the reading from the intended "edge-on" detector is twice the reading of the intended "side-on" detector), then the intended radial orientation of such cell was in fact effected, the cell was illuminated properly (e.g., from a lateral side) and the reading from the detector established to detect EMR emitted out the lateral side of the cell (again, a lateral side of a flow orthogonal cell cross section) can be used to make a conclusion as to an intrinsic characteristic of the cell (e.g., whether the cell is X chromosome-bearing or Y chromosome-bearing).

Such conventional "two orthogonal detector" protocol relies on the well-known artifact effect where, e.g., the intensity of EMR emitted out the edge of a flow orthogonal cross-section of the head of a sperm cell as a result of a lateral side impinging illumination of such cell is twice as great as that of EMR emitted out the lateral side of a flow orthogonal cross-section of the head of such sperm cell as a result of such illumination. In general, the basic full radial orientation assurance protocol is an effective manner by to determine whether a detector reading is reliable; it is, in fact, employed in aspects of the inventive technology. However, the conventional EMR projector and detector configuration—while adequate to determine when a cell is fully radially oriented—does not address the problem of how to generate reliable readings from cells that are not fully radially oriented. Aspects of the inventive technology disclosed herein seek to achieve reliable readings from cells that, using conventional systems, would go to waste (because, of course, their less than full radial orientation renders detector readings unreliable). As such, aspects of the inventive technology may reduce waste as compared with conventional technologies. Aspects of the inventive technology, particularly those that seek to increase the percentage of analyzed cells as to which reliable conclusions regarding an intrinsic cell characteristic (again, every cell that is illuminated and whose emitted EMR is detected, regardless of whether such cell is fully oriented is considered an analyzed cell), may enable retrofitting of conventional flow cytometers so as to increase such percentage.

Additional aspects of the inventive technology address cell illumination configurations in which at least one additional electromagnetic radiation projector is located downflow of a "most upflow", or first EMR projector, where all such projectors (e.g., a reflector or an EMR source) are established to effect the cell illumination by projecting electromagnetic radiation at the cell. Such "axially spaced illumination" embodiments of the inventive technology, which, similarly to the "off-axis" detector technologies, may find particular application not only to analysis systems that seek to fully radially orient cells, but also to systems that do not seek to fully radially orient cells. Indeed, aspects of the inventive "axially spaced illumination" technology, particularly those in which EMR projectors define flow orthogonal projector axes that together define a non-zero angle (i.e., where the axes, again, each in an axially separated flow orthogonal plane, when overlayed, define a non-zero angle) may be able to reduce the percentage of cells that are wasted in radially orienting systems; where a sufficient number of such axially spaced EMR projectors are so established, acceptable percentages of cells as to which reliable emitted EMR detection results cells may be obtained even in non-orienting systems.

As such, at least one embodiment of the inventive technology seeks to reduce the percentage of cells that are wasted in radially orienting analysis systems.

At least one embodiment of the inventive technology seeks to reduce the percentage of cells that are wasted in analysis systems that do not seek to radially orient cells.

At least one embodiment of the inventive technology seeks to enable retrofitting of existing radially orienting systems so as to reduce the percentage of cells that are wasted, perhaps by 10% to 20%.

A goal of at least one embodiment of the inventive technology is to provide an analysis system that obtains reliable emitted EMR detector readings from cells from that prior art systems are unable to reliably detect.

A goal of at least one embodiment of the inventive technology is to provide a multiple illumination system configured so as to illuminate cells from various angles, thereby either: obtaining reliable emitted EMR readings from cells that, in radially orienting systems, would otherwise proceed to waste; or obtaining acceptable percentages of analyzed cells having reliable EMR readings in analysis systems that do not seek to radially oriented cells.

A goal of at least one embodiment of the inventive technology is to provide a multiple illumination system that illuminates cells only to the extent necessary.

A goal of at least one embodiment of the inventive technology is to obtain reliable detector readings—readings that can be used to yield accurate information relative to an intrinsic cell characteristic—from a cell whose radial orientation is from 10 to 45 degrees away from full radial orientation.

Of course, other goals and advantages of the inventive technology are revealed in the disclosure provided herein, whether explicitly or implicitly.

DISCLOSURE OF INVENTION

Particular embodiments of the inventive technology relate to "off-axis detector" technology that employs a third detector exhibiting a flow orthogonal axis that is from 30 degrees to 60 degrees from an intended, flow orthogonal, cell cross section long axis alignment line, in addition to employing a fourth detector whose flow orthogonal axis is orthogonal to that of the third detector. Particular embodiments of the inventive technology relate to "axially spaced illumination" technology featuring more than one cell illumination site, where, other than the most upflow illumination site, all illumination site(s) are downflow of at least one other illumination site. Particular embodiments of the inventive technology may feature both technologies.

MODES FOR CARRYING OUT THE INVENTION

Figures 1A, 1B:
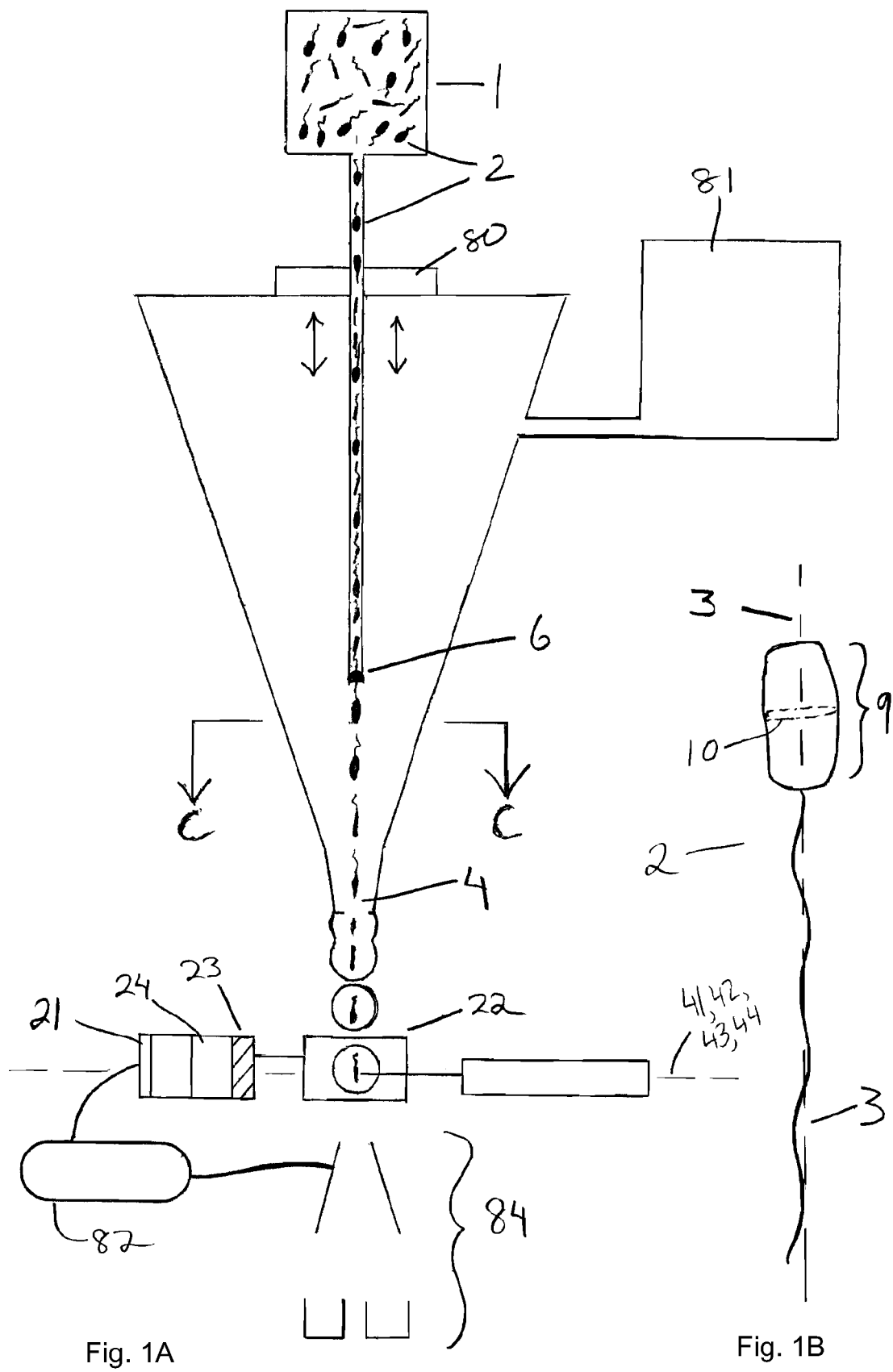
FIG. 1A shows an embodiment of the off-axis detector technology (flow axis appearing vertically on the page).
FIG. 1B shows a sperm cell, one of the many types of cells that may be analyzed by apparatus or according to methods of the inventive technology.

As mentioned earlier, the present inventive technology includes a variety of aspects, which may be combined in different ways. The following descriptions are provided to list elements and describe some of the embodiments of the present invention. These elements are listed with initial embodiments, however it should be understood that they may be combined in any manner and in any number to create additional embodiments. The variously described examples and preferred embodiments should not be construed to limit the present invention to only the explicitly described systems, techniques, and applications. Further, this description should be understood to support and encompass descriptions and claims of all the various embodiments, systems, techniques, methods, devices, and applications with any number of the disclosed elements, with each element alone, and also with any and all various permutations and combinations of all elements in this or any subsequent application.

A particular aspect of the inventive technology, which may be referred to as off-axis detector technology, may be described (in at least one embodiment) as a cell analysis apparatus (e.g., a flow cytometer, whether jet-in-air or other type) that comprises a cell source 1 that includes a plurality of cells 2 to be analyzed, each cell defining a cell long axis 3; a channel 4 (e.g., an orienting nozzle tip 5 and/or beveled injection needle 6 that may form an orienting nozzle; or a microfluidic channel 7) that defines a flow axis 8 and through which the cells flow; wherein the cells, when the cell long axis is parallel with the flow axis, have at least a portion 9 that has a flow orthogonal, cell cross-section 10 (a cross-section of the cell that is orthogonal to the flow when the cell long axis is parallel with the flow axis) that is non-circular. The flow orthogonal, cell cross-section may have a flow orthogonal, cell cross-section long axis 11 and a flow orthogonal, cell cross-section short axis 12 that is, typically, orthogonal to the flow orthogonal, cell cross-section long axis 11. It should be noted that a cell long axis is that cell axis which aligns with a unidirectional flow when the cell is carried by such flow. Further, the term axis, as used in any of the various contexts herein, does not necessarily imply symmetry thereabout; axes, as used herein, may, in instances, be at least conceptually infinite in length. It is also of note that a flow cytometer may be viewed as employing microfluidic principles, but it is not the case that all apparatus employing microfluidic principles are flow cytometers (for example flow cytometers typically employ drop-type analysis, but many microfluidic-based apparatus do not, as often, in a microfluidic channel, analysis is performed in-channel). As such, the term microfluidic channel, as used herein, should be understood to include (in non-limiting fashion) channels in which cell analysis is performed therein.

Further, in the off-axis detector technology, the channel 4 may define an intended, flow orthogonal, cell cross section long axis alignment line 13 and an intended, flow orthogonal, cell cross section short axis alignment line 14 that may be orthogonal to the intended, flow orthogonal, cell cross section long axis alignment line. The term "intended" may indicate that it may be the case that (as is found in most orienting apparatus) fewer than all cells passing through an orienting channel are oriented such that their flow orthogonal, cell cross section long axis aligns with such alignment line (although the intent may be that all cells passing therethrough are so oriented). In this aspect of the inventive technology, the channel may be configured to orient the cells so that each cell presents at full orientation during a cell illumination, wherein, when the cell is in the full orientation: (a) the cell long axis is parallel with the flow axis, (b) the flow orthogonal, cell cross-section long axis is aligned with the intended flow orthogonal, cell cross section long axis alignment line, and (c) the flow orthogonal, cell cross-section short axis is aligned with the intended, flow orthogonal, cell cross section short axis alignment line.

Figure 2:
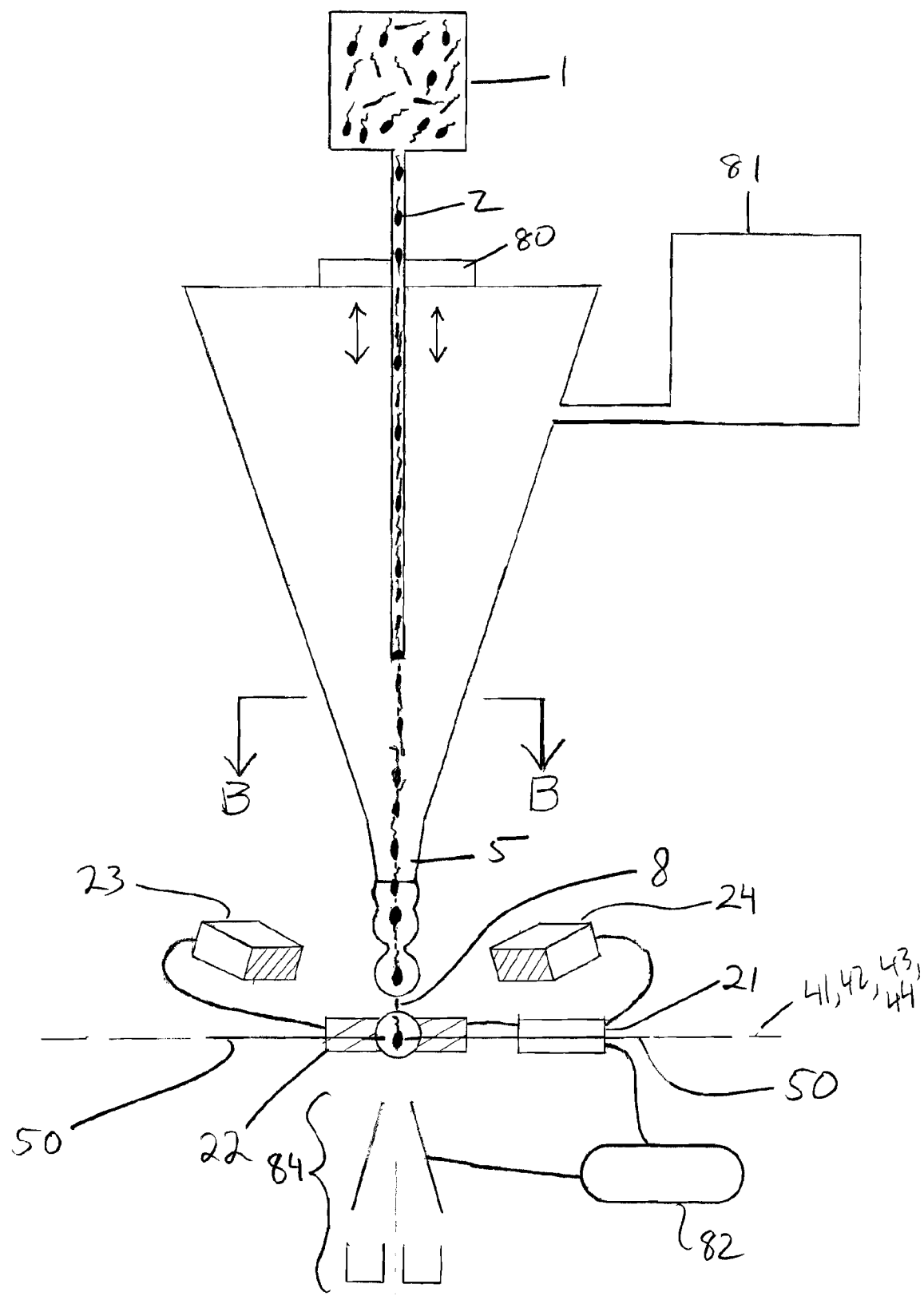
FIG. 2 shows an embodiment of the off-axis detector technology; the third and fourth EMR detectors are configured to not collect any EMR traveling in a flow orthogonal plane (flow axis appearing vertically on the page).
Figure 3:
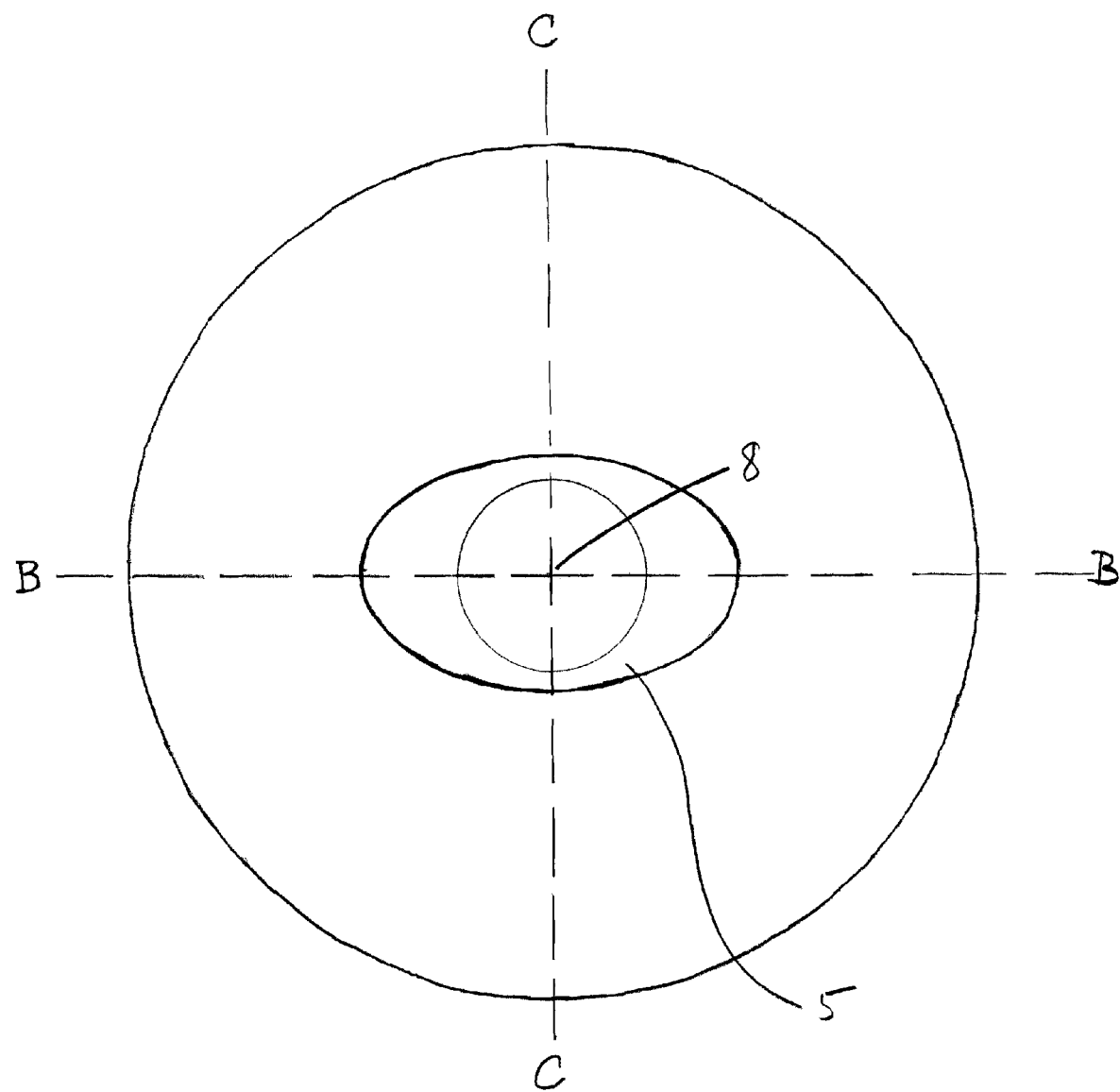
FIG. 3 shows a cross section of an orienting nozzle when viewed from above down the flow axis (flow axis into the page).
Figure 4:
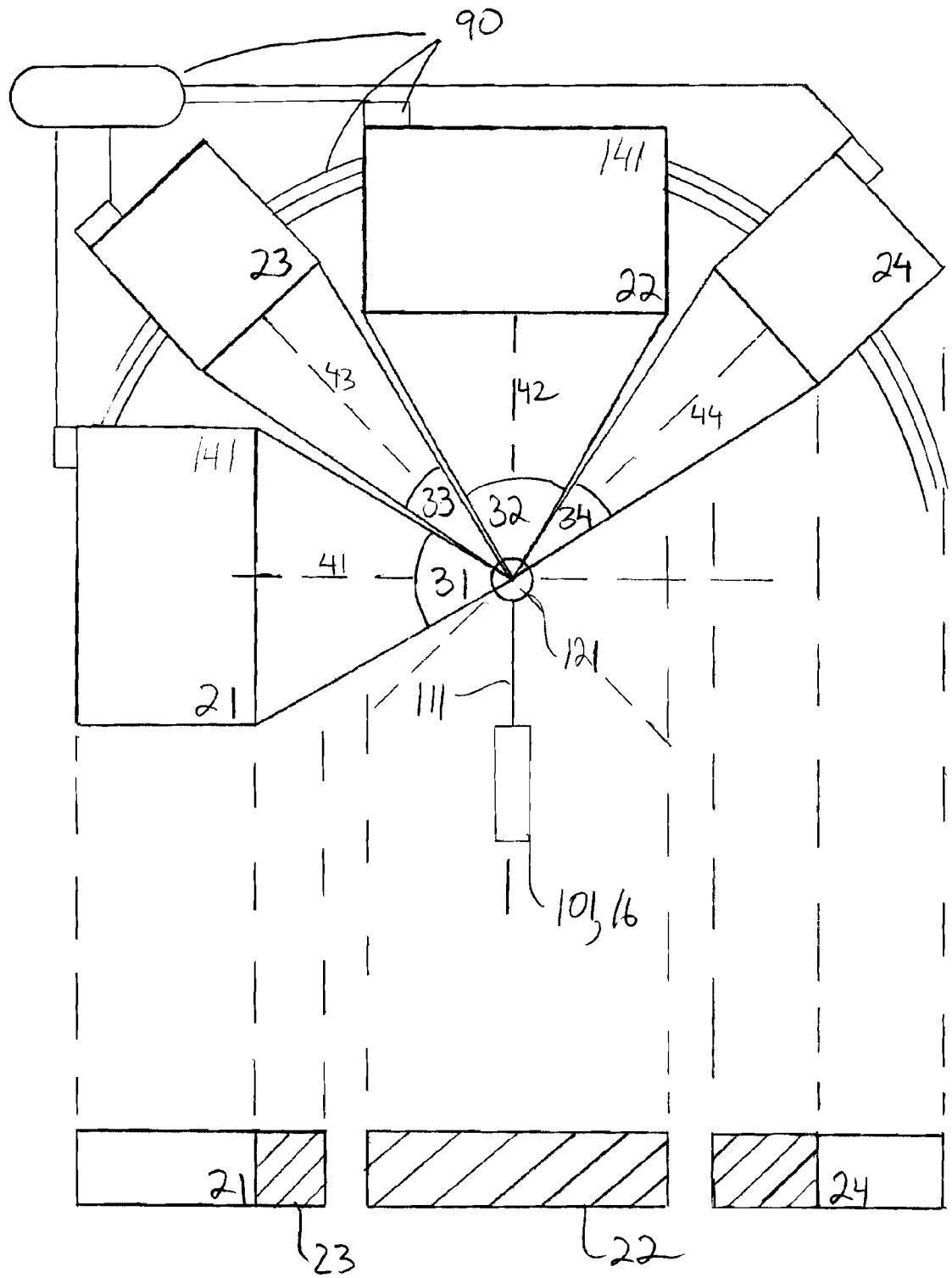
FIG. 4 shows an aerial plan view (above), with the flow axis into the page, and a projected side view associated therewith (below), of detectors in a flow orthogonal plane and as may be configured about an illumination site in a possible embodiment of the inventive off-axis detector technology or the inventive axially spaced illumination technology. Of course, particularly as relates to the inventive axially spaced illumination technology, such illumination site may be one of a plurality of axially spaced illumination sites.
Figure 6:
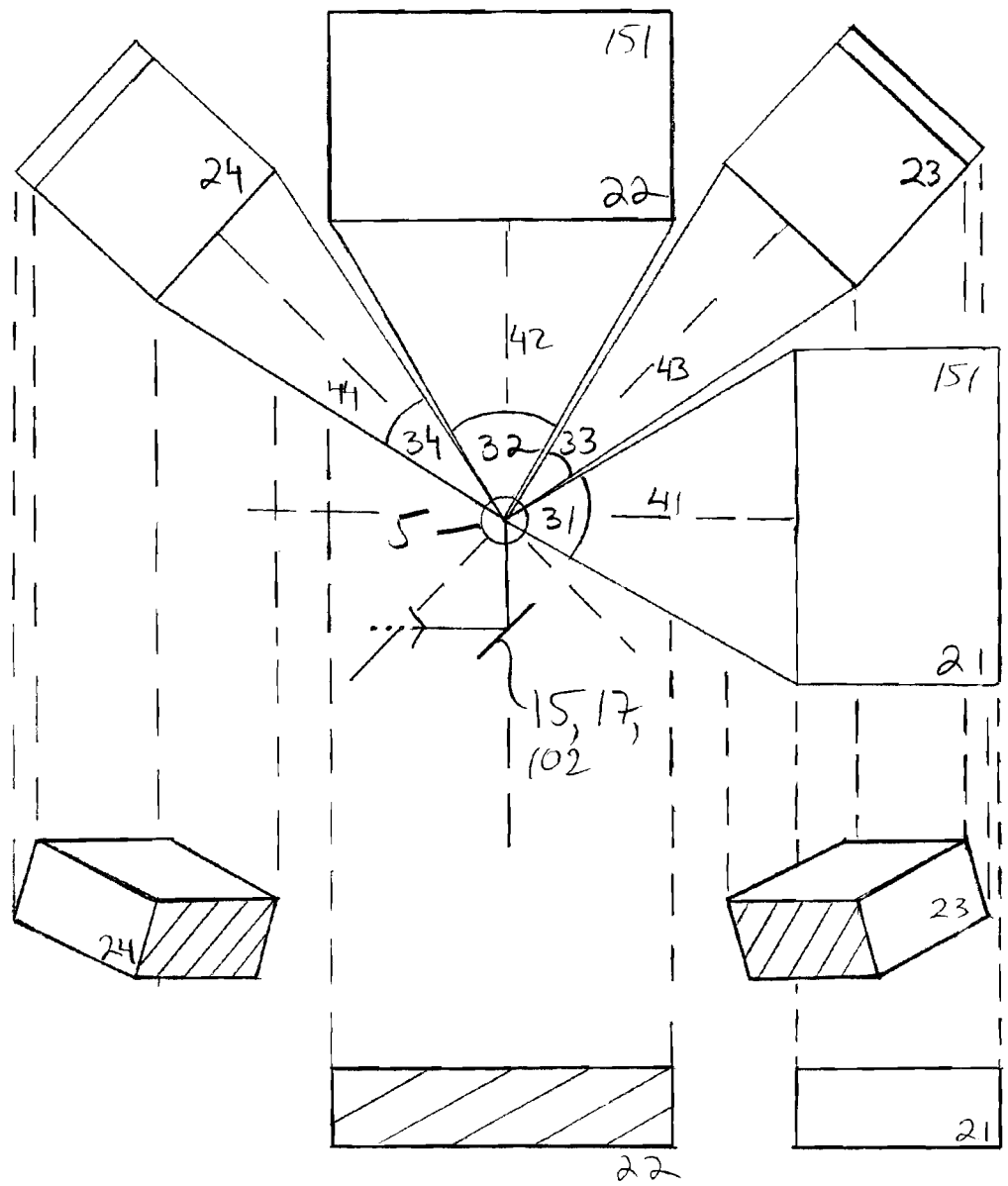
FIG. 6 shows an aerial plan view (above), with the flow axis into the page, and a projected side view associated therewith (below), of detectors in a flow orthogonal plane and as may be configured about an illumination site in a possible embodiment of the inventive off-axis detector technology or the inventive axially spaced illumination technology. Of course, particularly as relates to the inventive axially spaced illumination technology, such illumination site may be one of a plurality of axially spaced illumination sites.
Figure 7:
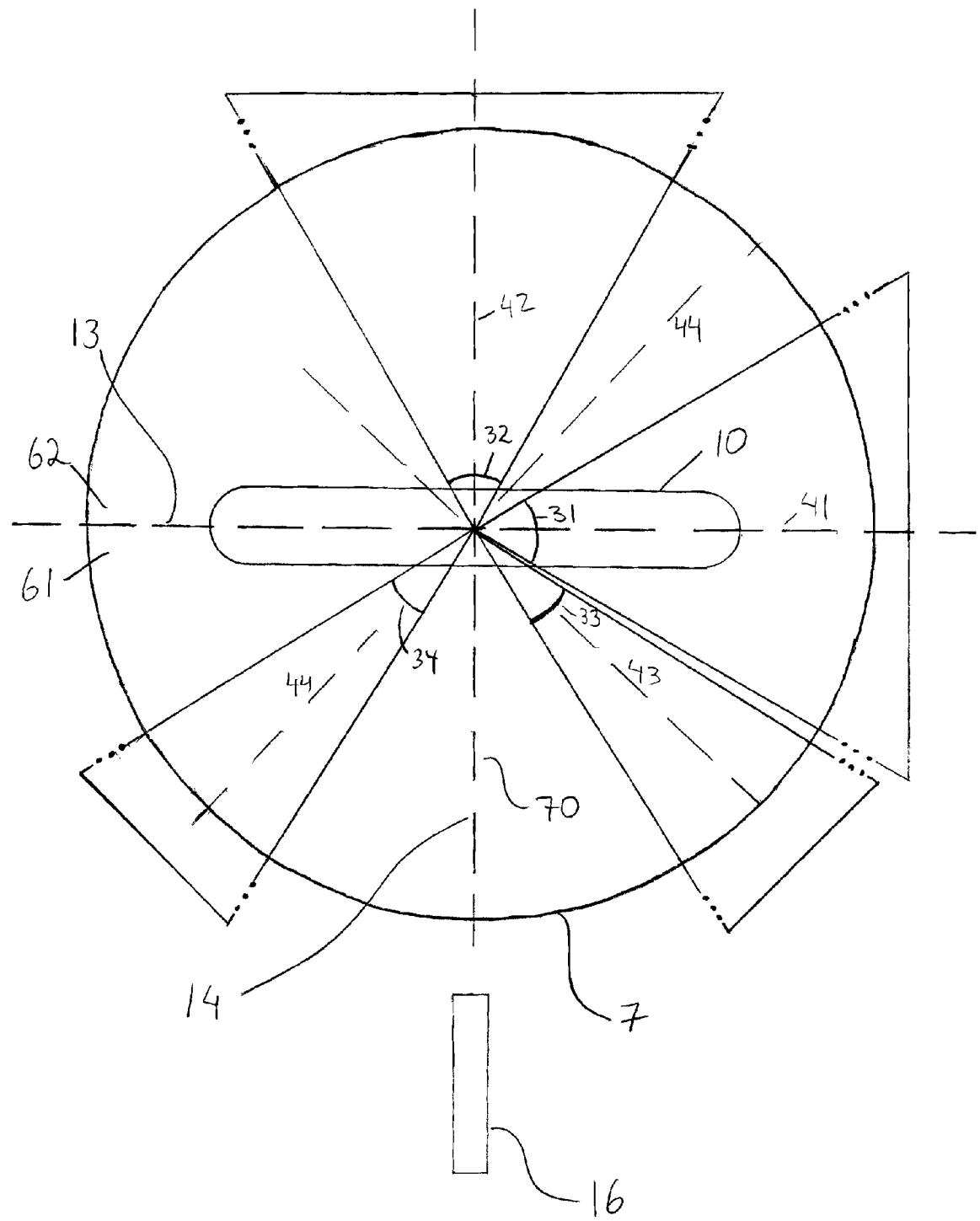
FIG. 7 shows collection angles of EMR detectors as they may be configured relative to a fully radially oriented cell, in a flow orthogonal plane, at an illumination site (with flow axis into the page) in a possible embodiment of the inventive off-axis detector technology or the inventive axially spaced illumination technology. Of course, particularly as relates to the inventive axially spaced illumination technology, such illumination site may be one of a plurality of axially spaced illumination sites. In this and FIGS. 8 through 13, the outer circle shown can be either a drop cross section or a microfluidic channel cross-section. At the center of such circle (FIGS. 7-13) is shown a cell cross-section (with its two lateral sides, one above the other) and its two edges (both joining the lateral sides, one edge on the right and one on the left)). Of course, this is only a representative cell cross-section geometry; analyzed cells may take many possible shapes, and certainly are not limited to the shape shown. Further, in the same vein, lateral sides need not be flat as shown and edges need not be semicircular as shown.
Figure 8:
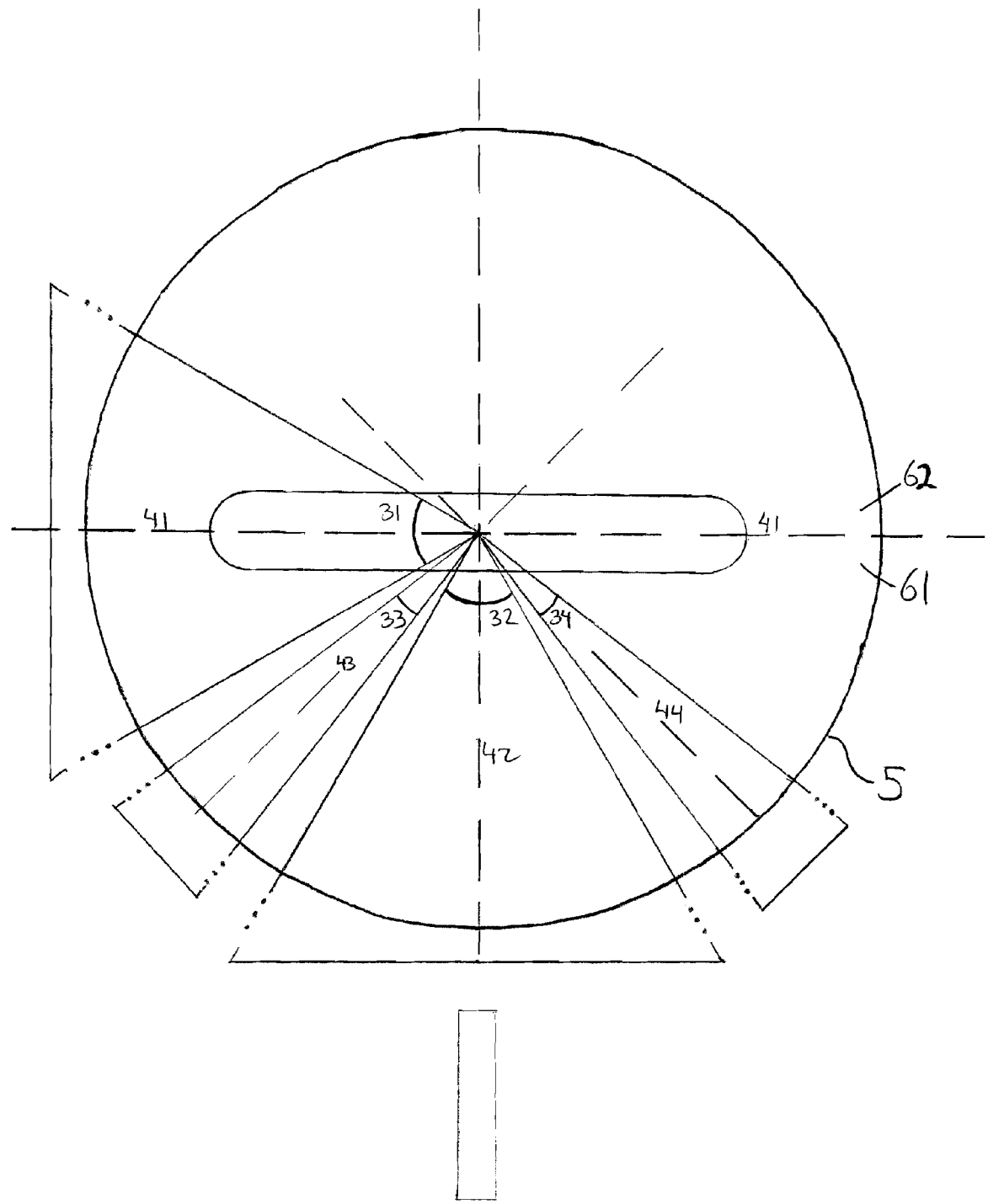
FIG. 8 shows collection angles of EMR detectors as they may be configured relative to a fully radially oriented cell, in a flow orthogonal plane, at an illumination site (with flow axis into the page) in a possible embodiment of the inventive off-axis detector technology or the inventive axially spaced illumination technology. Of course, particularly as relates to the inventive axially spaced illumination technology, such illumination site may be one of a plurality of axially spaced illumination sites.
Figure 9:
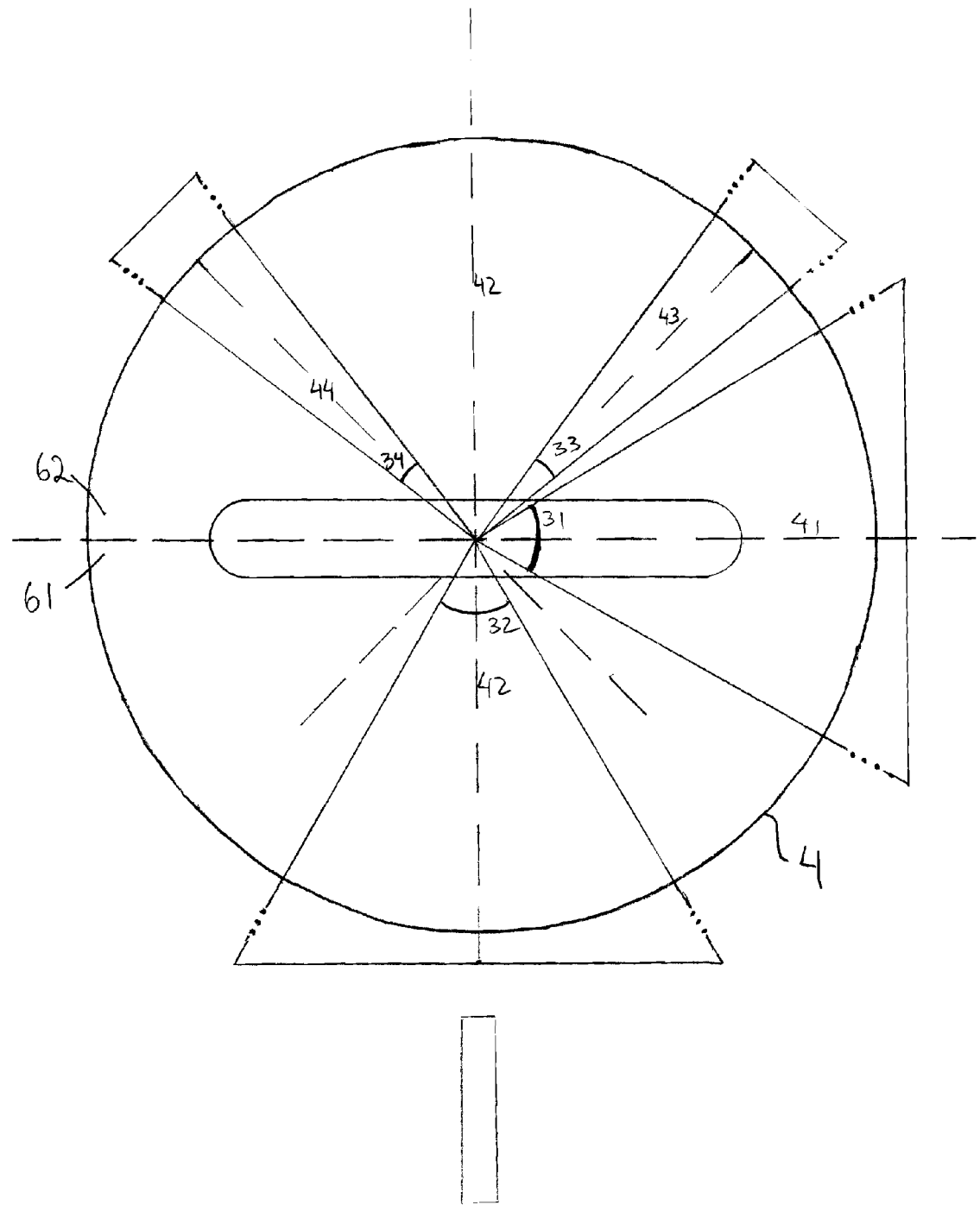
FIG. 9 shows collection angles of EMR detectors as they may be configured relative to a fully radially oriented cell, in a flow orthogonal plane, at an illumination site (with flow axis into the page) in a possible embodiment of the inventive off-axis detector technology or the inventive axially spaced illumination technology. Of course, particularly as relates to the inventive axially spaced illumination technology, such illumination site may be one of a plurality of axially spaced illumination sites.
Figure 10:
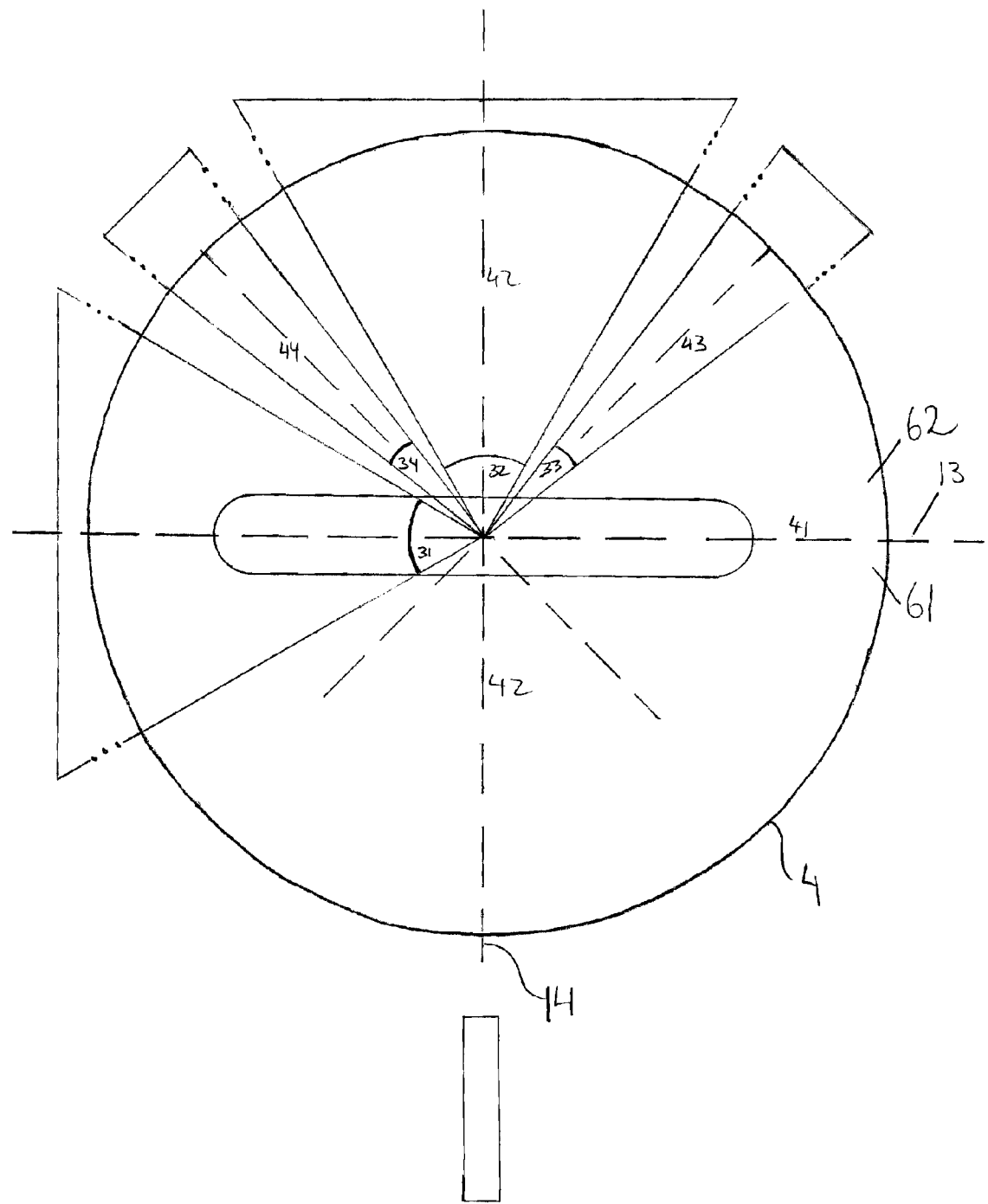
FIG. 10 shows collection angles of EMR detectors as they may be configured relative to a fully radially oriented cell, in a flow orthogonal plane, at an illumination site (with flow axis into the page) in a possible embodiment of the inventive off-axis detector technology or the inventive axially spaced illumination technology. Of course, particularly as relates to the inventive axially spaced illumination technology, such illumination site may be one of a plurality of axially spaced illumination sites.
Figure 11:
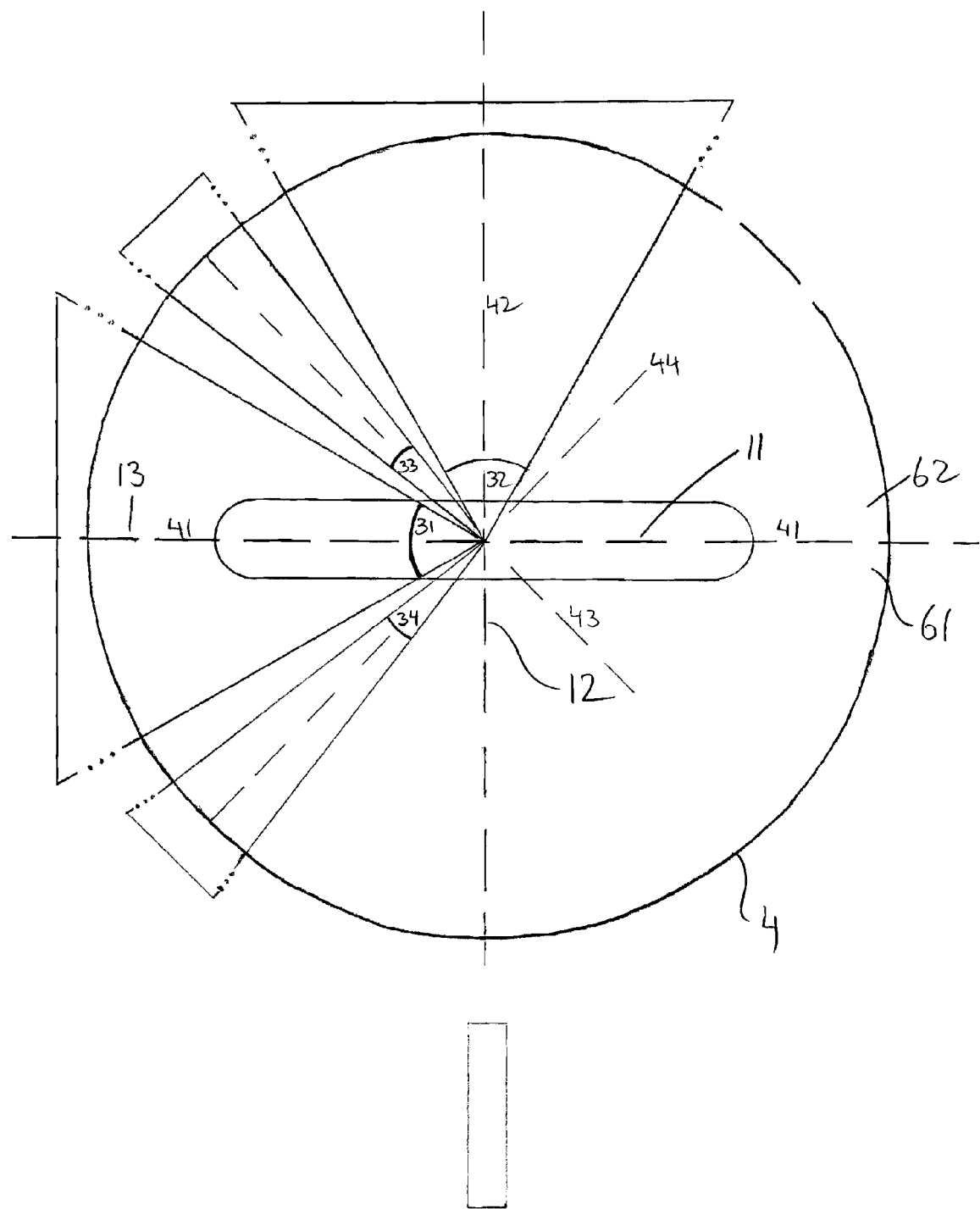
FIG. 11 shows collection angles of EMR detectors as they may be configured relative to a fully radially oriented cell, in a flow orthogonal plane, at an illumination site (with flow axis into the page) in a possible embodiment of the inventive off-axis detector technology or the inventive axially spaced illumination technology. Of course, particularly as relates to the inventive axially spaced illumination technology, such illumination site may be one of a plurality of axially spaced illumination sites.
Figure 12:
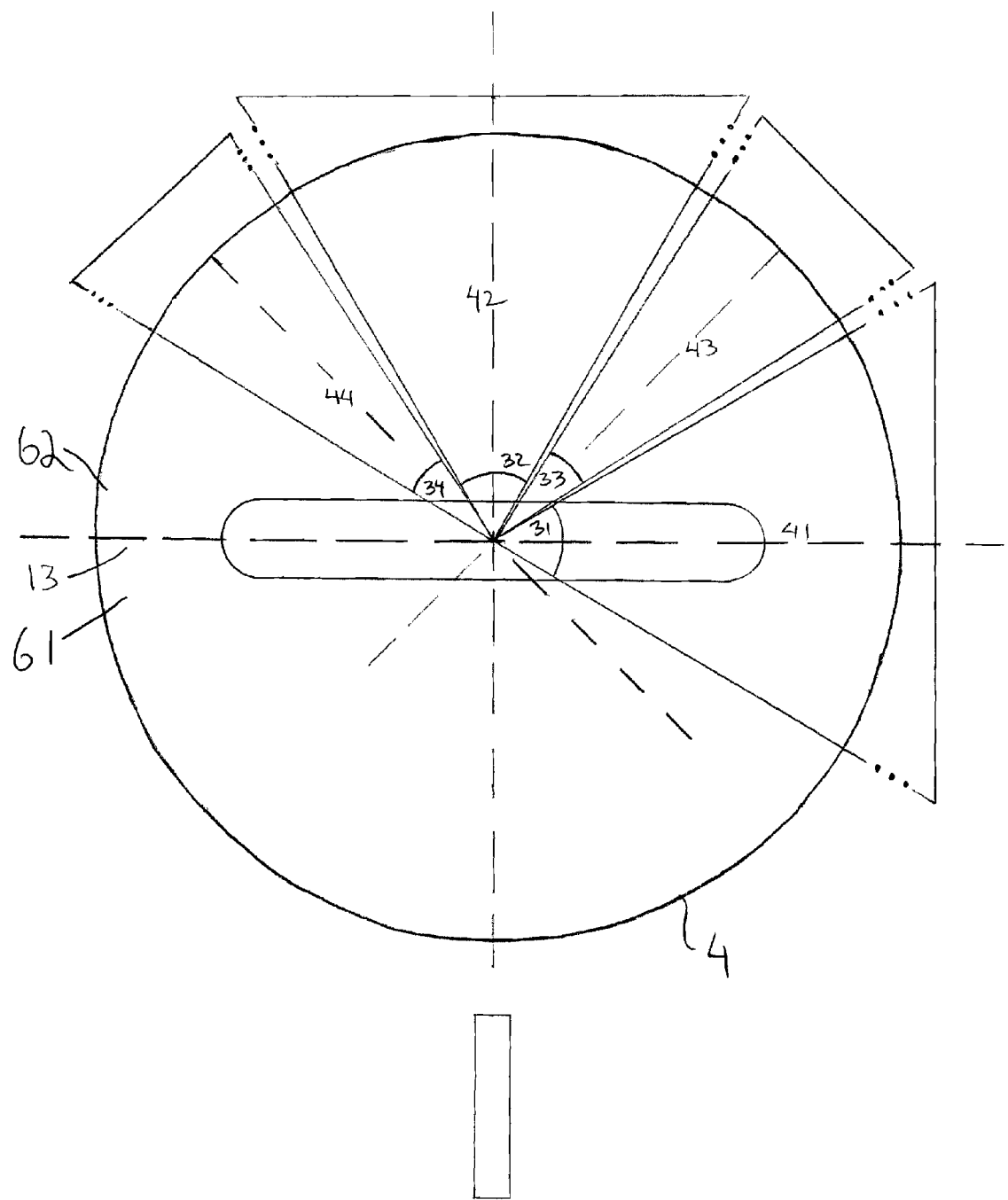
FIG. 12 shows collection angles of EMR detectors as they may be configured relative to a fully radially oriented cell, in a flow orthogonal plane, at an illumination site (with flow axis into the page) in a possible embodiment of the inventive off-axis detector technology or the inventive axially spaced illumination technology. Of course, particularly as relates to the inventive axially spaced illumination technology, such illumination site may be one of a plurality of axially spaced illumination sites.
Figure 13:
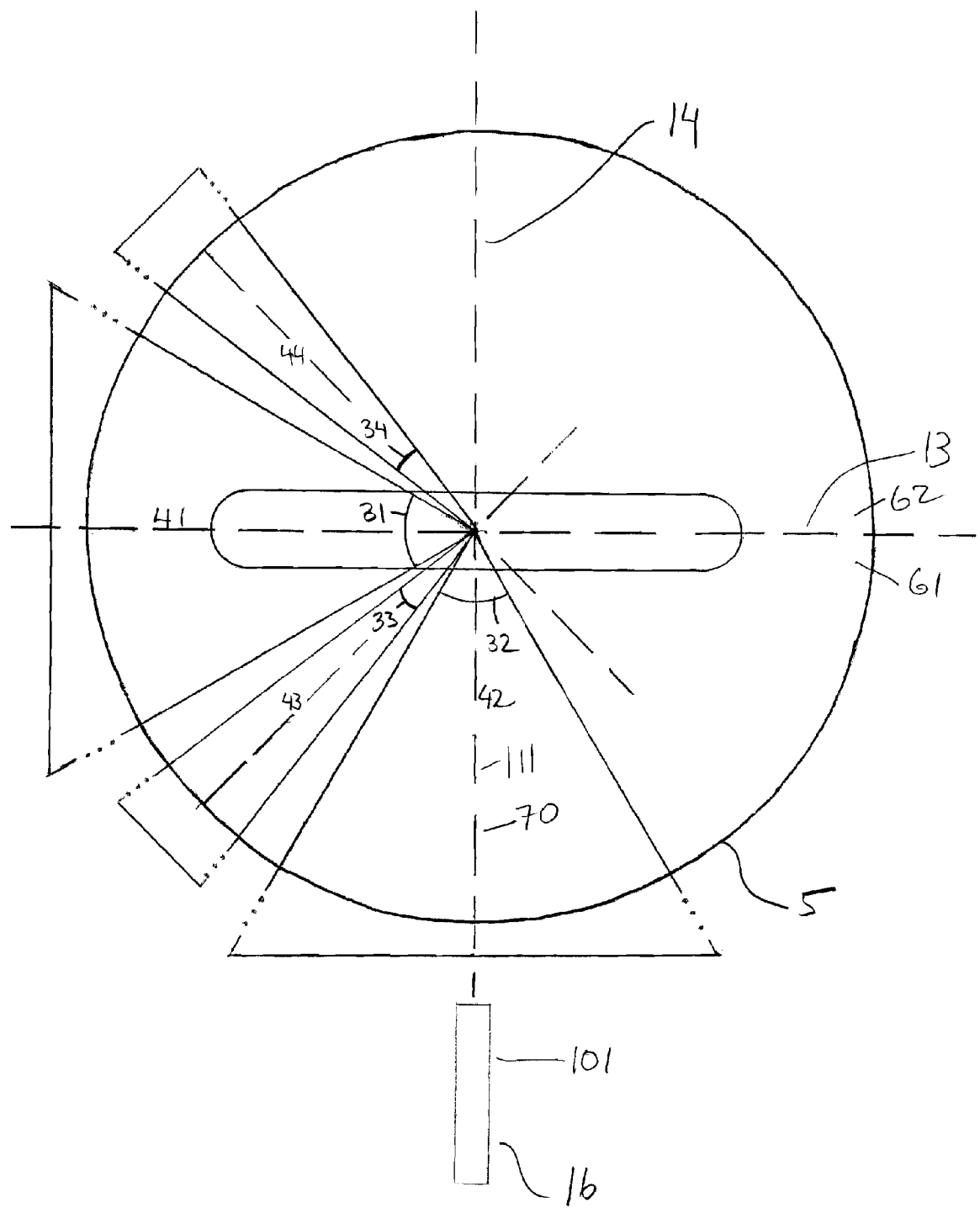
FIG. 13 shows collection angles of EMR detectors as they may be configured relative to a fully radially oriented cell, in a flow orthogonal plane, at an illumination site (with flow axis into the page) in a possible embodiment of the inventive off-axis detector technology or the inventive axially spaced illumination technology. Of course, particularly as relates to the inventive axially spaced illumination technology, such illumination site may be one of a plurality of axially spaced illumination sites.
Figure 14:
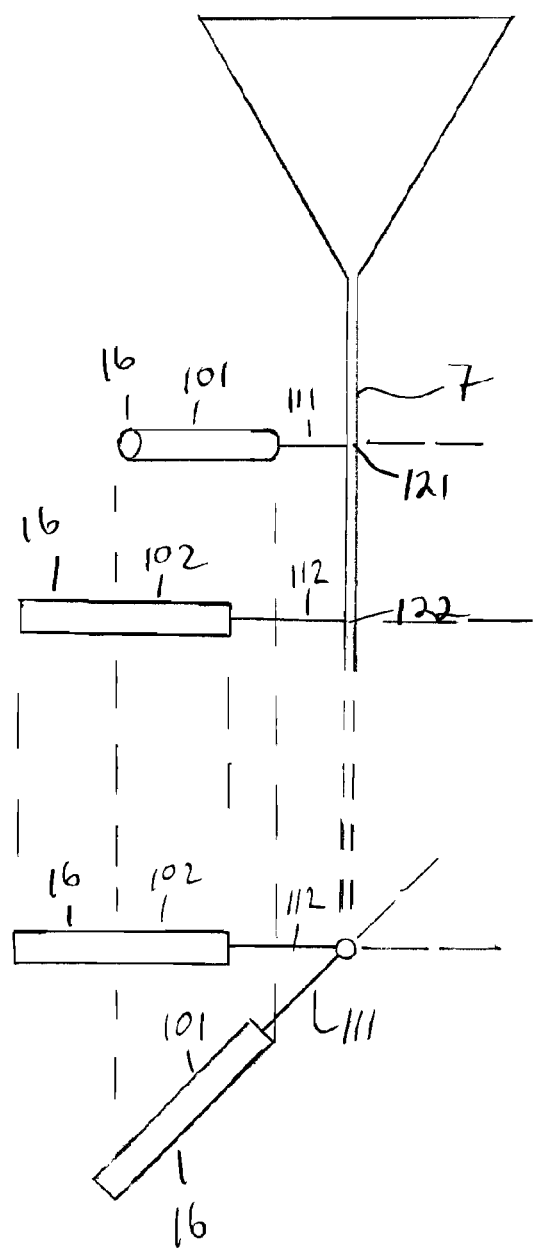
FIG. 14 shows a side view (above) of an embodiment of a microfluidic version of the inventive axially spaced illumination technology (flow axis appears vertically on the page), in addition to a projected aerial plan view (below, where the flow axis is into the page). In versions having EMR detectors associated with each illumination site, the detectors in FIG. 14 may be configured as shown in, e.g., any of the FIGS. 1, 2 and 4 through 13, in addition to being configured according to a conventional two mutually orthogonal detector set-up.
Figure 15:
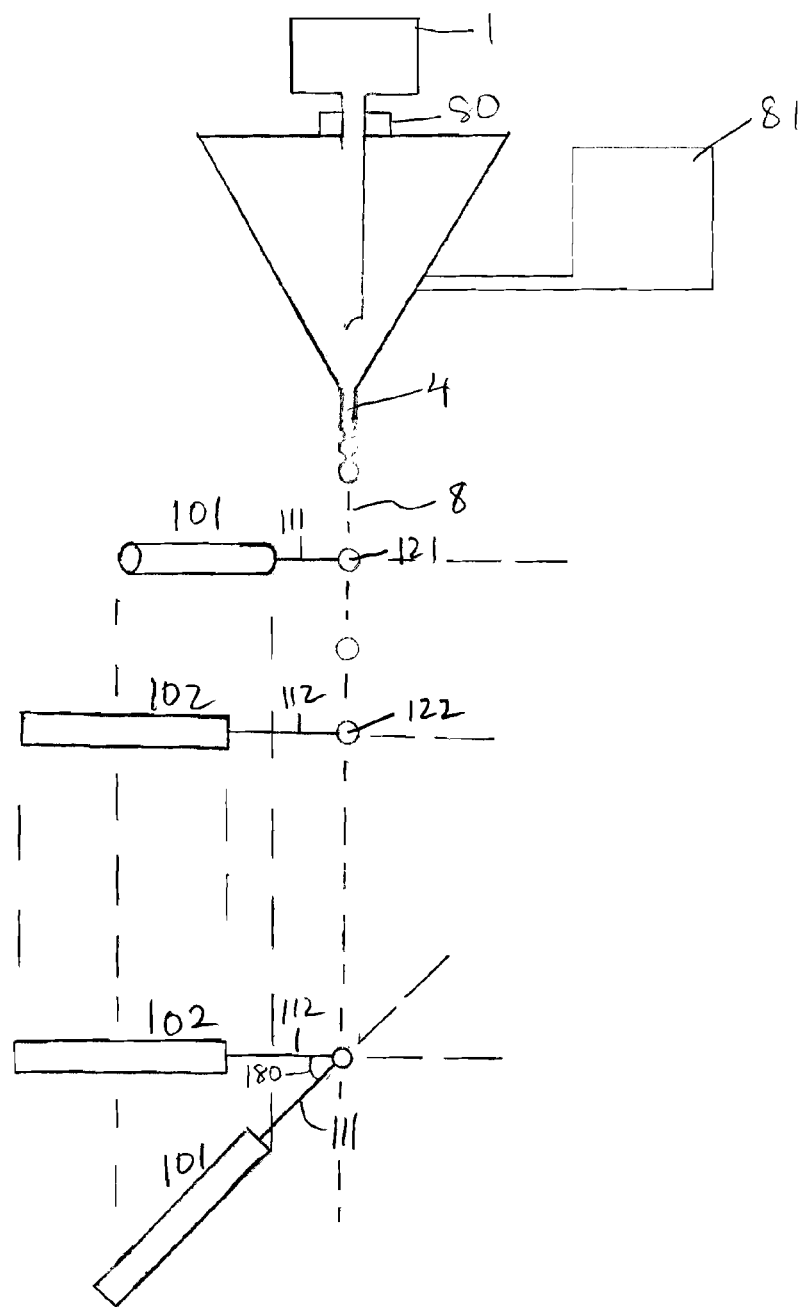
FIG. 15 shows a side view (above) of an embodiment of a jet-in-air flow cytometer version of the inventive axially spaced illumination technology (flow axis appears vertically on the page), in addition to a projected aerial plan view (below, where the flow axis is into the page). For clarity reasons, detectors and a cell analysis system are not shown. The cell analysis system may be, e.g., as shown in FIGS. 1A and 2 (as but one example of a possible sorting system). Detectors associated with each illumination site in FIG. 15 may be configured as shown in, e.g., any of the FIGS. 1,2 and 4 through 13, in addition to being configured according to a conventional two mutually orthogonal detector set-up.
Figure 16:
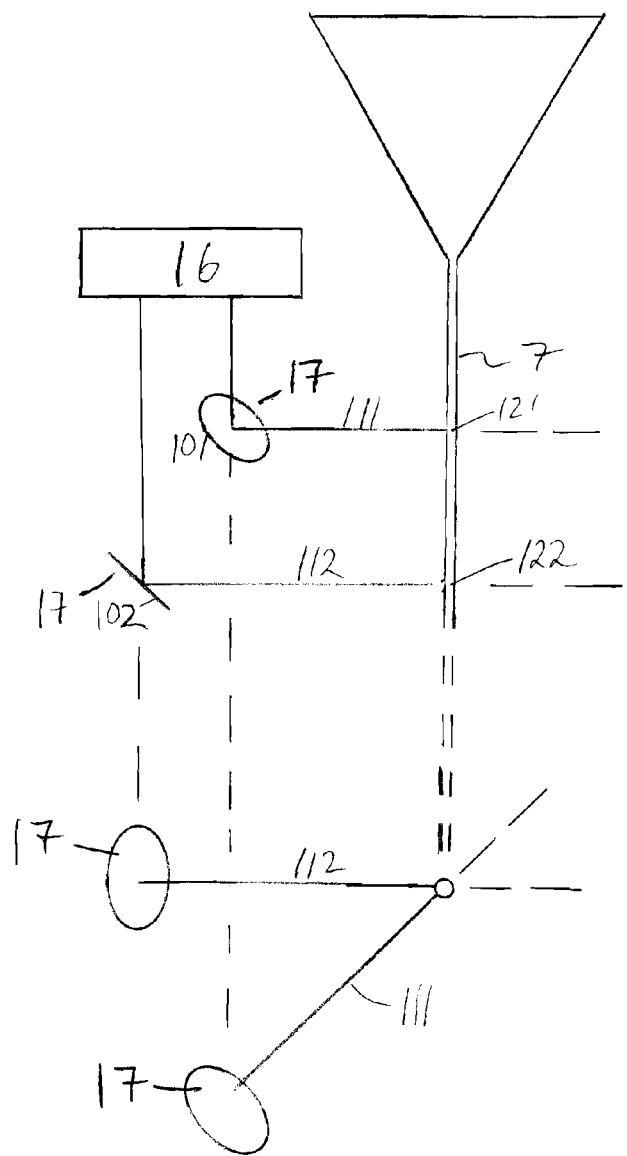
FIG. 16 shows a side view (above) of an embodiment of a microfluidic version of the inventive axially spaced illumination technology (flow axis appears vertically on the page), in addition to a projected aerial plan view (below, where the flow axis is into the page). In versions having EMR detectors associated with each illumination site, the detectors in FIG. 16 may be configured as shown in, e.g., any of the FIGS. 1,2 and 4 through 13, in addition to being configured according to a conventional two mutually orthogonal detector set-up.
Figure 17:
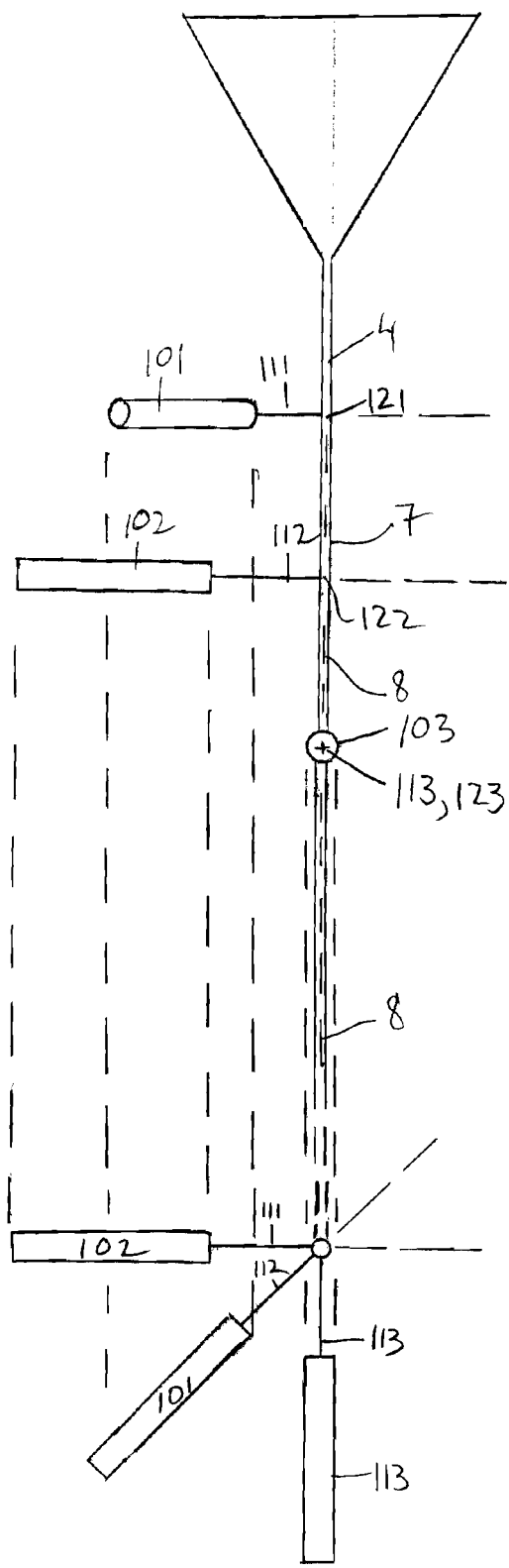
FIG. 17 shows a side view (above) of an embodiment of a microfluidic version of the inventive axially spaced illumination technology (flow axis appears vertically on the page), in addition to a projected aerial plan view (below, where the flow axis is into the page). In versions having EMR detectors associated with each illumination site, the detectors in FIG. 17 may be configured as shown in, e.g., any of the FIGS. 1,2 and 4 through 13, in addition to being configured according to a conventional two mutually orthogonal detector set-up.
Figure 18:
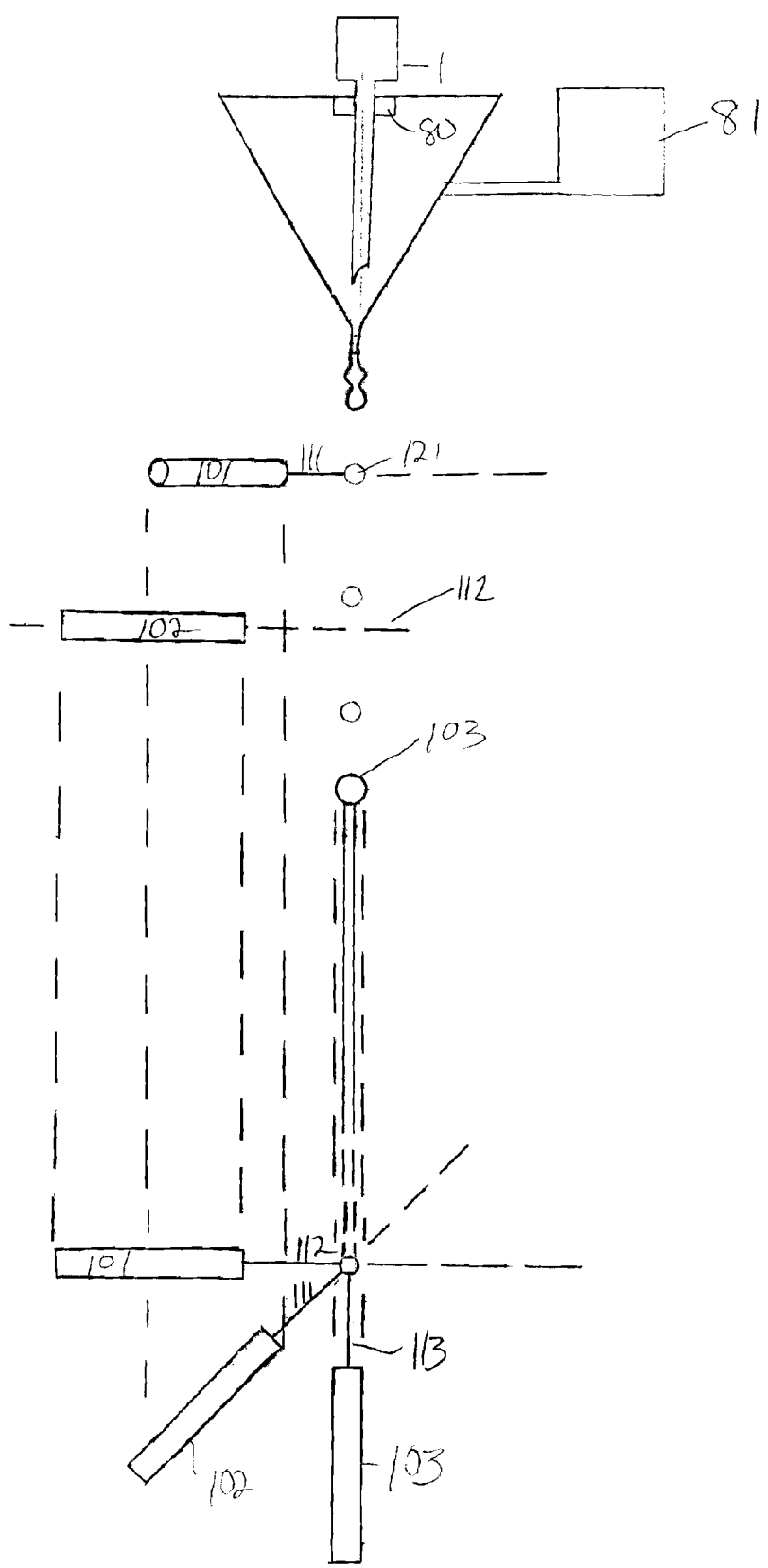
FIG. 18 shows a side view (above) of an embodiment of a jet-in-air flow cytometer version of the inventive axially spaced illumination technology (flow axis appears vertically on the page), in addition to a projected aerial plan view (below, where the flow axis is into the page). For clarity reasons, detectors and a cell analysis system are not shown. The cell analysis system may be, e.g., as shown in FIGS. 1A and 2 (as but one example of a possible sorting system). Detectors associated with each illumination site in FIG. 18 may be configured as shown in, e.g., any of the FIGS. 1,2 and 4 through 13, in addition to being configured according to a conventional two mutually orthogonal detector set-up.
Figure 19:
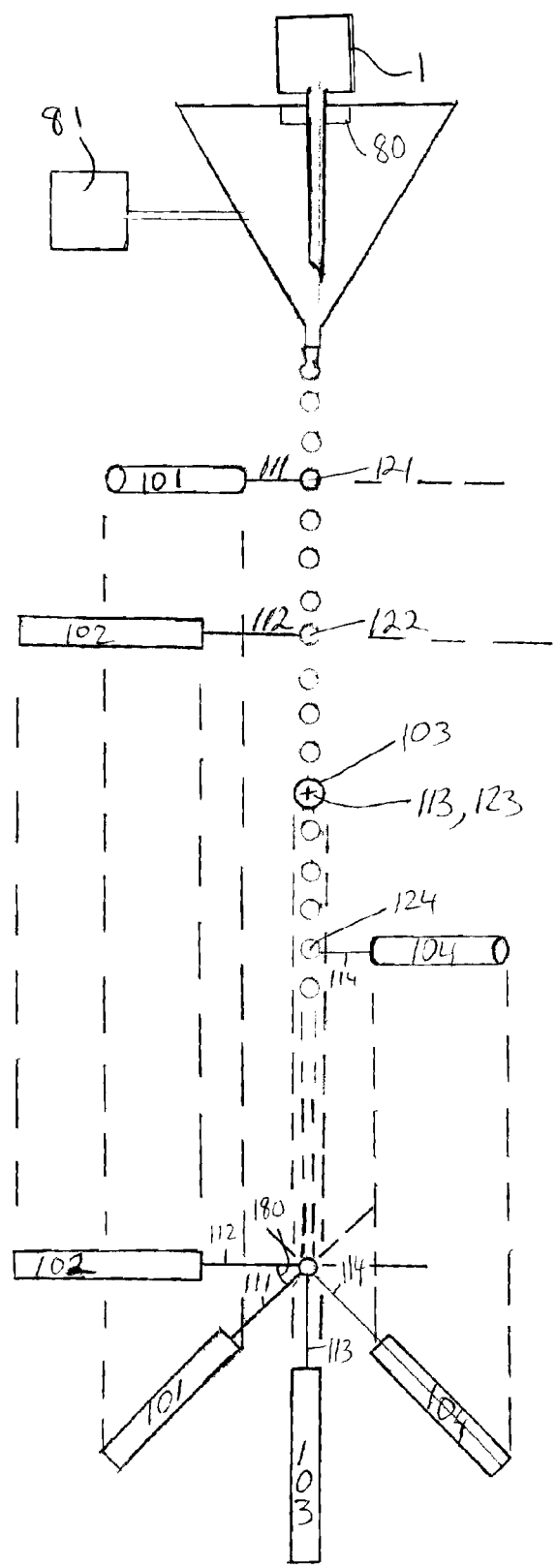
FIG. 19 shows a side view (above) of an embodiment of a jet-in-air flow cytometer version of the inventive axially spaced illumination technology (flow axis appears vertically on the page), in addition to a projected aerial plan view (below, where the flow axis is into the page). For clarity reasons, detectors and a cell analysis system are not shown. The cell analysis system may be, e.g., as shown in FIGS. 1A and 2 (as but one example of a possible sorting system). Detectors associated with each illumination site in FIG. 19 may be configured as shown in, e.g., any of the FIGS. 1,2 and 4 through 13, in addition to being configured according to a conventional two mutually orthogonal detector set-up.
Figure 20:
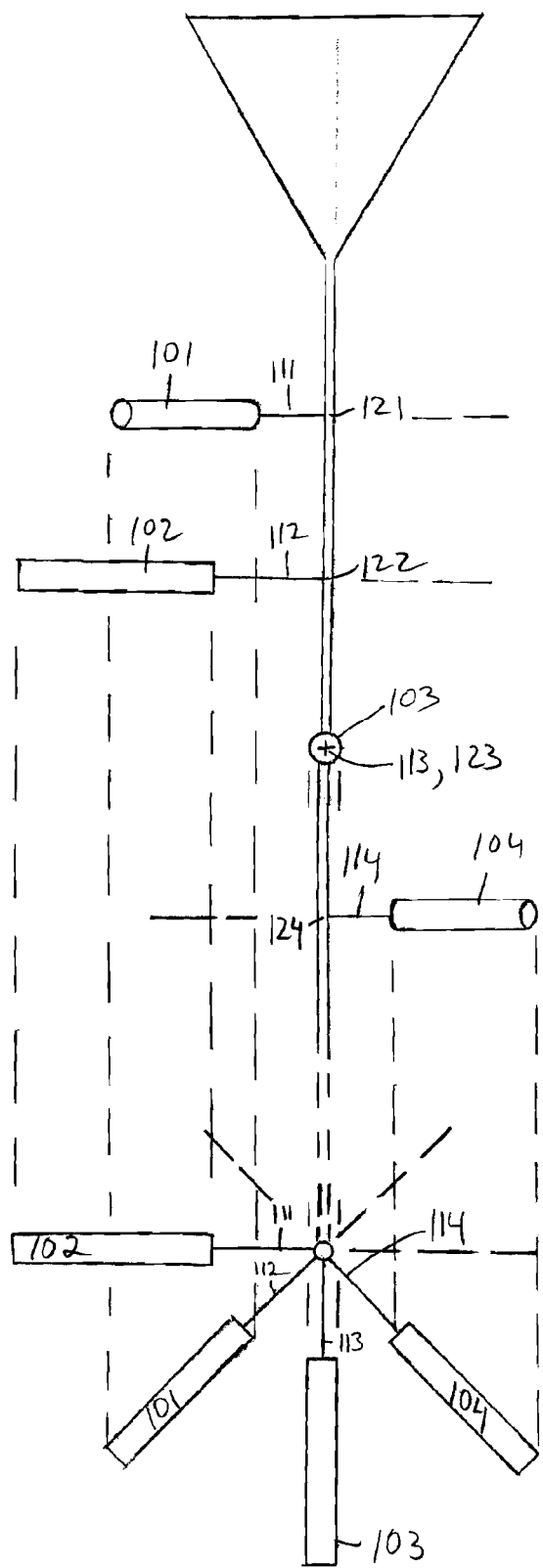
FIG. 20 shows a side view (above) of an embodiment of a microfluidic version of the inventive axially spaced illumination technology (flow axis appears vertically on the page), in addition to a projected aerial plan view (below, where the flow axis is into the page). In versions having EMR detectors associated with each illumination site, the detectors in FIG. 20 may be configured as shown in, e.g., any of the FIGS. 1,2 and 4 through 13, in addition to being configured according to a conventional two mutually orthogonal detector set-up.

The off-axis detector technology apparatus may further comprise an electromagnetic radiation projector 15 (e.g., EMR source 16 or EMR reflector 17) established to effect the cell illumination by projecting electromagnetic radiation at the cells, and a first EMR detector 21 and a second EMR (electromagnetic radiation) detector 22, each established to detect EMR emitted as a result of the cell illumination, wherein the first EMR detector has a first detector, flow orthogonal collection angle 31 that defines a flow orthogonal, first detector axis 41 and the second EMR detector 22 has a second detector, flow orthogonal collection angle 32 that defines a flow orthogonal, second detector axis 42. EMR detectors may include, inter alia, aperture (which may include a lens), filter(s) and a PMT. It is of note that the detector, flow orthogonal collection angle refers to: (a) the projection of the collection angle onto a flow orthogonal plane 50 when that light collected by the EMR detector does not travel in such plane (see, e.g., FIGS. 2 and 6); (b) the collection angle itself where that light collected by the EMR detector does travel in such flow orthogonal plane; and/or (c) a weighted average of collection angles when the associated detector collects EMR expressed over a range of collection angles (as where the detector face that receives EMR is triangular or circular (as but two examples), depending on the detectors' shapes and configuration. The axes defined by collection angles simply bisect such angles; the axes are conceptually infinite in length and, as such, do not terminate at the cell or in the center of any circle (or other figure) defined by the flow. Typically, the flow orthogonal, first detector axis 41 is substantially coaxial with the intended, flow orthogonal, cell cross section long axis alignment line 13, the flow orthogonal, second detector axis 42 is substantially coaxial with the intended, flow orthogonal, cell cross section short axis alignment line 14, and the flow orthogonal, first detector axis 41 and the flow orthogonal, second detector axis 42 may be substantially 90 degrees apart. It is of note that the above-described apparatus (i.e., one that includes, inter alia, a first and second EMR detector) may be retrofit to include third and fourth EMR detectors 23, 24 as described below. As such, this above-described apparatus (i.e., the oriented cell, two-detector apparatus), may be the focus of a retrofit procedure described further below.

The off-axis detector technology apparatus typically comprise a third EMR detector 23 and a fourth EMR detector 24, each established to detect EMR emitted as a result of the cell illumination; the third EMR detector 23 may have a third detector, flow orthogonal collection angle 33 that defines a flow orthogonal, third detector axis 43 and the fourth EMR detector 24 may have a fourth detector, flow orthogonal collection angle 34 that defines a flow orthogonal, fourth detector axis 44, and the flow orthogonal, third detector axis 43 and the flow orthogonal, fourth detector axis 44 may be substantially 90 degrees apart. Further, in this aspect of the inventive technology, the flow orthogonal, third detector axis 43 may be from 30 degrees to 60 degrees (e.g., 45 degrees, as but one example), or perhaps 20-45 degrees, from the intended, flow orthogonal, cell cross section long axis alignment line (hence the moniker "off-axis detector"); of course, such line extends across the cross-section.

In the off-axis detector technology apparatus and the flow cytometer retrofit method, one or more of each the first and second, and the third and fourth EMR detector 21, 22, 23, 24 may collect EMR traveling in a flow orthogonal plane 50 (often in addition to also collecting EMR traveling in a direction that is not flow orthogonal), because they are so established. Otherwise, one or more of each the detectors (particularly the third and the fourth) might not collect any EMR traveling in a direction orthogonal to the flow (see, e.g., FIGS. 2 and 6). The intended, flow orthogonal, cell cross section long axis alignment line 13 may define a first side 61 (e.g., a 180 degree "half disc" viewed from above) on which is established the electromagnetic radiation projector 15, and a second side 62. In certain embodiments, the flow orthogonal, second detector axis 42 may be on the first side 61; in others, it may be on the second side 62. So too may each the flow orthogonal, third detector axis 43 and the flow orthogonal, fourth detector axis 44 be on the either the first 61 or the second side 62.

Whether the apparatus is configured so that such detector axes are on one side or the other may depend on whether there are fore/aft optical artifacts (e.g., where EMR emitted (whether fluoresced or reflected) from the lateral side of a sperm head cross-section in a direction towards the EMR projector is different from EMR emitted (whether fluoresced EMR or EMR that simply passes through the cell without absorption and excitation) from the lateral side of a sperm cell head cross-section in a direction away from the EMR projector). Such artifacts, when present, may be significant enough (e.g., where EMR emitted out one lateral side of a sperm cell head cross section is not approximately half the EMR emitted out the edge of such cross section) such that a single protocol used to assess whether an analyzed cell is fully radially oriented is no longer appropriate for both such situations (e.g., where the detector aligned with the intended, flow orthogonal cell cross section short axis alignment line is on the first side 61 or the second side 62). If the effect results in predictable, repeatable detector readings for fully radially oriented cells (e.g., where EMR emitted out the lateral side of a sperm head cross-section in a direction towards the EMR projector is always 0.8 times EMR emitted out the lateral side of a sperm cell head cross-section in a direction away from the EMR projector) then perhaps a different protocol (e.g., a protocol other than one that tests for the presence of EMR emitted out the lateral side of a sperm head cross section that is twice that of EMR emitted out the edge) may be used. However, some cells may not exhibit such differential excitation response, and a single protocol may be used regardless of whether the second detector axis 42 is on the first side 61 or the second side 62.

Figure 5:
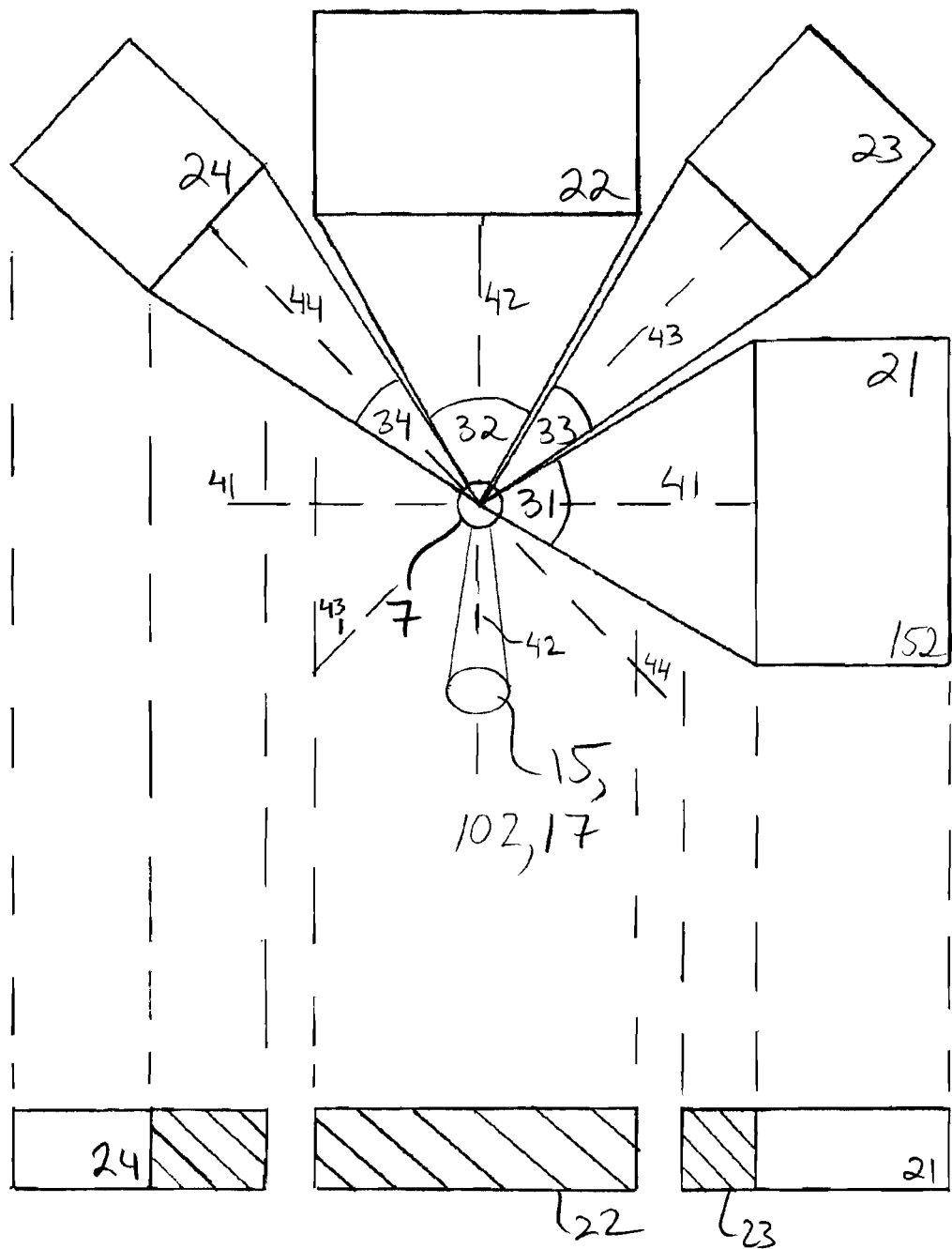
FIG. 5 shows an aerial plan view (above), with the flow axis into the page, with the flow axis into the page, and a projected side view associated therewith (below), of detectors in a flow orthogonal plane and as may be configured about an illumination site in a possible embodiment of the inventive off-axis detector technology or the inventive axially spaced illumination technology. Of course, particularly as relates to the inventive axially spaced illumination technology, such illumination site may be one of a plurality of axially spaced illumination sites.

In the "off-axis detector technology" apparatus and the flow cytometer retrofit method, typically, the first EMR detector 21 may detect to provide information relative to the cell orientation and the second EMR detector 22 may detect to provide information relative to an intrinsic cell characteristic. For such reason, they may be each characterized as having unitary functionality. The third EMR detector 23 may detect to provide information relative to the cell orientation at one point in time and information relative to an intrinsic cell characteristic at another point in time; the fourth detector 24 may also exhibit such dual functionality, both perhaps depending on the improperly radially oriented cell's direction of rotation (clockwise of counterclockwise in a flow orthogonal plane 50) away from full radial orientation. This, again, is in contrast to the unitary functionality of the first and second EMR detectors 21, 22 and may arise from the configuration of the flow orthogonal, third and fourth detector axes 43, 44 relative to the flow orthogonal, projector axis 70 and, more particularly, the symmetry of such detector axes about such projector axis. Further, in particular embodiments, the cell illumination may occur after the cell has exited the channel (e.g., where the apparatus is a jet-in-air flow cytometer as in FIG. 1A); in a microfluidic system (see, e.g., FIG. 5), typically the cell illumination occurs when the cell is in the channel.

In the case where the cells to be analyzed are sperm cells, the intrinsic cell characteristic may be X or Y chromosome (i.e., whether the cell bears an X or Y chromosome). Perhaps the cells are stained to effect differential illumination response such as differential fluorescence; such stains include, but are not limited to, those that bind DNA in an manner that is not sex-specific (i.e., non-sex specific stains, e.g., an appropriate Hoechst stain such as Hoechst 33342, as is well known, where relative amounts of fluorescence from DNA labeled thereby may be in proportion to DNA mass), or stains that stain only the X chromosome, or, on the other hand, only the Y chromosome (i.e., sex-specific stains, a broad term that includes sequence specific polyamides and sex-specific antibodies). Sex specific antibodies may be used to label the sperm cells in a staining mixture. For example, a sex specific antibody may be conjugated with a fluorescent moiety (or equivalent reporter molecule). Because the antibody binds to antigens present on only an X chromosome-bearing or, alternatively, a Y chromosome-bearing cell, such cells can be selectively identified based upon their fluorescence (versus the non-fluorescence of an unlabeled cell). Moreover, more than one sex specific antibody, each antibody having a different fluorescent moiety attached thereto, may be used simultaneously. This allows for differentiation of X chromosome-bearing and Y chromosome-bearing cells based upon the differing fluorescence of each.

All inventive technologies disclosed herein (particularly those not incorporating microfluidics) may relate to apparatus that may further comprise an oscillator 80 established to oscillate the cells; it may further comprise a sheath fluid reservoir 81; it may further comprise an electronic data analysis system 82 (e.g., a digital data analysis system 83 such as a computerized data analysis system that processes in some fashion numerical data such as detector readings) to which readings from the EMR detectors are input. Electronic data analysis systems, particularly when incorporating digital electronics (i.e., a digital data analysis system), may facilitate the use of multi-channels, multi-detectors and even radial illumination that converges from substantially all points around a cell (e.g., 360 degree radial illumination) and, indeed, increase speed (e.g., cell throughput). Apparatus may further comprise a cell sorter 84 (e.g., electrostatic plates and receptacles; or, particularly in microfluidic systems, optical switches, rapid field-free electroosmotic micro-pump(s), or momentum transfer sorters, and sorting channels) typically established downflow of a site of the cell illumination. The electronic data analysis system may be configured to operate on readings (e.g., light intensity readings) from the detectors in order to determine whether reliable information relative to an intrinsic cell characteristic can be gleaned therefrom, perhaps by processing such readings (e.g., mutual comparisons, comparisons to predetermined values and/or mathematically manipulating such readings, whether through the preferred use of digital electronics such as digital pulse processing circuitry to process photodetector pulses from closely spaced cells or not). In at least one embodiment of the inventive technology, the electronic data analysis system may be configured to determine if there is a detector pair (typically, detectors in a pair will be mutually orthogonal) in which one of the detector readings is substantially twice the other reading; as is well known, when such is the case, the lower reading may be relied on to accurately determine information relative to an intrinsic cell characteristic.

Further, the electromagnetic radiation projector 15 may be established to effect cell illumination by projecting electromagnetic radiation at the cells and in a direction substantially parallel the intended, flow orthogonal, cell cross section short axis alignment line 13 (although indeed the EMR projector might not be so established). It is also of note that, in certain embodiments, the off-axis detector technology apparatus may be operational after a retrofit procedure is performed, perhaps on a flow cytometer that does not have a third and a fourth EMR detector associated with a single illumination (a two detector apparatus), as mentioned above.

As mentioned, an aspect of the inventive technology that may be particularly related to the off-axis detector technology may be described as a flow cytometer retrofit method. It may include, inter alia, the initial step of securing a flow cytometer for a retrofit procedure; that cell cytometer may be the oriented cell, two-detector apparatus described above. The step of securing the flow cytometer may comprise the step of clamping the flow cytometer and/or the step of simply establishing the flow cytometer before a retrofitter (e.g., a technician capable of performing a successful retrofit).

The aforementioned flow cytometer retrofit method may further comprise the steps of establishing (e.g., by mechanically and electrically "setting up") a third EMR detector 23 and a fourth EMR detector 24 to each detect EMR emitted as a result of the cell illumination. The third EMR detector 23 may have a third detector, flow orthogonal collection angle 33 that defines a flow orthogonal, third detector axis 43 and the fourth EMR detector 24 may have a fourth detector, flow orthogonal collection angle 34 that defines a flow orthogonal, fourth detector axis 44. The step of establishing a third EMR detector 23 and the fourth EMR detector 24 may comprise the step of establishing the third EMR detector 23 and the fourth EMR detector 24 so that: the flow orthogonal, third detector axis 43 and the flow orthogonal, fourth detector axis 44 are substantially 90 degrees apart, and the flow orthogonal, third detector axis 43 is from 30 degrees to 60 degrees (e.g., approximately 45 degrees, where approximately as used herein indicates within 3 degrees either way of the indicated number(s)) from the intended, flow orthogonal, cell cross section long axis alignment line 13.

It is of note that any apparatus reflecting either the off-axis detector technology or the axially spaced illumination technology (see below) may include controllably movable optics (e.g., motorized optics). In such embodiments, either the EMR projector(s) and/or the detectors may be controllable moved to desired positions (e.g., the relative angles of two or more of the flow orthogonal detector axes may be adjusted upon movement via motorized control 90 (whether computer controlled or otherwise)). Indeed, any sort of adjustment (displacement of a detector (e.g., its lens and or PMT) along or around a flow axis, radial positioning of an EMR projector within a flow orthogonal plane, as but a few examples), perhaps to improve analysis, can be effected via motorized control, which may include electronic control and a track, in one of several possible configurations.

An independent, but nonetheless related, aspect of the inventive technology may be referred to as focusing on "axially spaced illumination" (where "axially" refers to the flow axis) and may be described as a cell analysis apparatus that comprises a cell source 1 that includes a plurality of cells to be analyzed, a channel 4 that defines a flow axis 8 and through which the cells flow in a downflow direction (which may, but need not be a downward gravitational direction); a first electromagnetic radiation projector 101 defining a flow orthogonal, first projector axis 111 and established to effect a first cell illumination by projecting electromagnetic radiation at the cells at a first illumination site 121; at least one first illumination EMR detector 141 established so as to detect EMR emitted as a result of the first cell illumination; a second electromagnetic radiation projector 102 defining a flow orthogonal, second projector axis 112 and established to effect a second cell illumination by projecting electromagnetic radiation at the cells at a second illumination site 122; and at least one second illumination EMR detector established 151 so as to detect EMR emitted as a result of the second cell illumination, where the second illumination location is downflow of the first illumination location, and where the flow orthogonal, first projector axis 111 and the flow orthogonal, second projector axis (when such axes are overlain) define a non-zero angle 180 (e.g., approximately 45 degrees, approximately 90 degrees, or within the ranges (including endpoints) of from 44 degrees to 50 degrees, 40 degrees to 45 degrees, 38 degrees to 43 degrees, and from 34 to 41 degrees, as but a few of many possibilities). It is of note that a flow orthogonal, projector axis is the projection, onto a flow orthogonal plane 50, of the central axis of the EMR (whether in the form of a beam or otherwise) projected by an electromagnetic radiation projector; in such manner, an electromagnetic radiation projector defines the flow orthogonal, projector axis.

Of course, there may be more than two axially spaced illuminations, typically effected by more than two EMR projectors, each defining a respective flow orthogonal, projector axis. Such axes would typically not overlap. A preferred embodiment may involve a four illumination configuration with each projector defining an axis that is at 45 degrees to a most proximate projector axis. This may stem from the observation in some applications and using some cytometers, that illumination becomes ineffective when the projector axis defines a greater than about 45 degree angle with the flow orthogonal, cell cross section short axis. However, this is not the only possible configuration, as indeed three, five, six, seven and upwards projector systems, with various angles defined by projector axes, are possible and contemplated by the inventive technology. In certain designs, a "n" projector system will have "n" projectors defining "n" axes, where each axis is at approximately 180/n degrees from a most proximate axis.

In particular embodiments of the "axially spaced illumination" apparatus, the at least one first illumination EMR detector 141 may comprise two first illumination EMR detectors. Further, the channel may form at least part of an orienting flowpath, and the two first illumination EMR detectors may have collection angles that define flow orthogonal, first illumination detector axes. Such axes may be mutually orthogonal. Also, it is of note that the channel 4 may define an intended, flow orthogonal, cell cross section long axis alignment line 13, and one of the flow orthogonal, first illumination detector axes may be aligned with the intended, flow orthogonal, cell cross section long axis alignment line (particularly where the flow orthogonal, first projector axis is parallel with the intended, flow orthogonal, cell cross section long axis alignment line).

In particular embodiments of the "axially spaced illumination" apparatus, the at least one second illumination EMR detector 151 may comprise two second illumination EMR detectors (as such, two EMR detectors may detect illumination emitted as a result of the second illumination), and the channel may form at least part of an orienting flowpath. Further, the two second illumination EMR detectors may have collection angles that define flow orthogonal, second illumination detector axes; such axes may be mutually orthogonal. The channel may define an intended, flow orthogonal, cell cross section long axis alignment line 13, and one of the flow orthogonal, second illumination detector axes may be from 30 degrees to 60 degrees from the intended, flow orthogonal, cell cross section long axis alignment line (particularly where the flow orthogonal, second projector axis is from 30 to 60 degrees the intended, flow orthogonal, cell cross section long axis alignment line).

In at least one embodiment of the inventive "axially spaced illumination" apparatus, the at least one first illumination detector may comprise at least three first illumination detectors. At least one of the at least three first illumination detectors may collect EMR traveling in a direction that is not orthogonal to the flow. Further, the at least one second illumination detector may comprise at least three second illumination detectors, and at least one of the at least three second illumination detectors may collect EMR traveling in a direction that is not orthogonal to the flow.

Each axially spaced illumination (and the detector setup associated therewith) may feature any of the aspects of the aforementioned off-axis detector technology, particularly, of course, where the channel seeks to orient the cells (e.g., in the case of an orienting nozzle). As such, each illumination site may have associated therewith, in one exemplary embodiment, four detectors (as described above relative to the off-axis detector technology). Relative to the detectors associated with another immediately upflow or downflow illumination site, the detectors of a reference illumination site may be disposed at an angle (as projected onto a flow orthogonal plane) that mimics the relative angular disposition (also as projected onto a flow orthogonal plane) of the corresponding EMR projectors. As such, where a flow orthogonal, first projector axis 111 and a flow orthogonal, second projector axis 121 define a 45 degree angle, the flow orthogonal, first illumination detector axes may each form a 45 degree angle with each corresponding flow orthogonal, second illumination detector axes, particularly where each of the sets of detectors have the same configuration relative to their respective EMR projectors. Of course, this is only one of many possible configurations (some of which might not exhibit such "angle mimicking" design).

It is of note that at least one of the at least one first illumination detector 141 and the at least one second illumination detector 151 may collect EMR traveling in a flow orthogonal plane (although this is certainly not a requirement). Further, at least one of the at least one first illumination detector 141 and the at least one second illumination detector 151 may collect EMR traveling in a direction that is not orthogonal to the flow.

As with any EMR projector in any of the inventive technologies, the first EMR projector 101 may comprise a first EMR source and the second EMR projector comprises a second EMR source (e.g., laser, an arc lamp and a LED). As should be understood, an EMR projector is an object or device that projects EMR. As such, it may be a reflector such as a mirror, or an EMR source.

In particular "axially spaced illumination" embodiments, the first illumination and the second illumination may occur when the cell is in the channel (e.g., in microfluidic applications); in others (as where the cell analysis apparatus is a jet-in-air flow cytometer), the first illumination and the second illumination occur after the cell has exited the channel. Further, in certain embodiments, the second cell illumination (and any other downflow illuminations) can be precluded in response to information derived from readings of the at least one first illumination EMR detector; as one might expect, such second (and/or third, or fourth) illumination may be properly precluded when an immediately upflow illumination (e.g., the second illumination would be immediately upflow a third illumination) results in reliable detector readings (e.g., where the intensity reading of the first detector is twice that of the second detector). Of course, it may be the case where the earliest (e.g., most upflow) illumination to yield reliable results may be downflow the first (most upflow) illumination; in such case, as expected, only those illuminations that are further downflow of the earliest illumination yielding reliable results can be precluded. For example, where there are four illumination sites (a term which, it should be understood, requires only the capability to illuminate at such site), where the third illumination is the earliest to yield reliable detector readings, it may be possible to preclude only the fourth illumination. Of course, the rationale for limiting illumination is to mitigate, or avoid entirely, undesired, possibly harmful cell viability/health/effectiveness impacts attributed to excessive amounts of radiation.

It is also of note that the "axially spaced illumination" apparatus may further comprise a cell source 1 that includes a plurality of cells to be analyzed, an electronic data analysis system 82 to which readings from at least one of the EMR detectors are input, and a cell sorter 84 established downflow of the second cell illumination site 122 (which includes a design where, e.g., the illumination site that is most proximate the cell sorter is a third illumination site).

Importantly, and as mentioned, the "axially spaced illumination" technology can incorporate one or more features of the "off-axis detector technology." However, it is important to understand that an apparatus embodying the "axially spaced illumination" technology need not radially orient the cells in any fashion (although indeed cells may be oriented so that their long axis is parallel with the flow axis). In such non-oriented applications, ignoring concerns relative to over-radiating cells, four axially spaced EMR projectors, each emitting EMR projector having a flow orthogonal projector axis that is approximately 45 from a nearest flow orthogonal projector axis may be preferable. It is of note that FIGS. 14-20 show only a few of the many possible embodiments; other embodiments include, but are not limited to, those embodiments where one or more of the EMR projectors is established 180 degrees from where it is shown on such figures.

It is also of note that, although the "off-axis detector" inventive technology may indeed find application in apparatus embodying microfluidic technologies, it is the "axially spaced illumination" inventive technologies that may find a more pronounced microfluidic application than might the off-axis detector technology. As such, the term channel, as used herein, includes, but is not limited to, an orienting nozzle tip or a microfluidic channel.

It is of note that in any of the embodiments, the cells analyzed may be sperm cells (whether non-human animal such as bull sperm, or other), or indeed, any of a number of types of aspherical cells. Further, in any of the "off-axis detector" or "axially spaced illumination" embodiments (again, some apparatus may embody both technologies), the apparatus as claimed may be one of several such apparatus in a parallel sorting device (whether such device is microfluidic or conventional cytometer-based).

A method that relates directly to the "axially spaced illumination" may be referred to as a cell analysis method and may comprise the steps of: establishing a cell source that includes a plurality of cells to be analyzed, passing the cells through a channel that defines a flow axis and in a downflow direction; establishing a first electromagnetic radiation projector 101 so as to effect a first cell illumination by projecting electromagnetic radiation at the cells at a first illumination site 121, wherein the first electromagnetic radiation projector defines a flow orthogonal, first projector axis 111; establishing at least one first illumination EMR detector 141 so as to detect EMR emitted as a result of the first cell illumination; establishing a second electromagnetic radiation projector 102 so as to effect a second cell illumination by projecting electromagnetic radiation at the cells at a second illumination site 122, wherein the second electromagnetic radiation projector defines a flow orthogonal, second projector axis 112, establishing at least one second illumination EMR detector 151 so as to detect EMR emitted as a result of the second cell illumination, wherein the second illumination location is downflow of the first illumination location, and wherein the flow orthogonal, first projector axis and the flow orthogonal, second projector axis define a non-zero angle 180. Additional steps may relate to the establishment of a third electromagnetic radiation projector 103 so as to effect a third cell illumination by projecting electromagnetic radiation at the cells at a third illumination site 123 that is downflow of the second illumination site 112. Of course, other features of this inventive method technology may be as described above relative to the "axially spaced illumination" apparatus.

Particular embodiments of the inventive technology may be described as a cell analysis apparatus (e.g., a flow cytometer or a microfluidic-based apparatus) that comprises a radially orienting channel 5 and/or 6 that radially orients a cell passing therethrough and that defines an intended, flow orthogonal, cell cross section long axis alignment line 13; an EMR projector 15 that projects EMR at said cell to effect a cell illumination; an EMR detector configuration that includes a plurality of EMR detectors 21, 22 (and others perhaps) able to detect EMR emitted as a result of said cell illumination and that is able to generate a reliable detected EMR reading; and an electronic analysis system 82 which uses said reliable detected EMR reading to generate accurate information about an intrinsic cell characteristic, wherein said EMR detector configuration is able to obtain such reliable detected EMR reading when a flow orthogonal, cell cross section long axis 11 and said intended, flow orthogonal, cell cross section long axis alignment line 13 form an angle that is from zero to 45 degrees. Conventional flow cytometers simply may not be able to accurately analyze cells that are "misoriented" (radially) to such an extent. Such inventive apparatus may use a scheme and elements described in the off-axis detector technology". Apparatus employing aspects of the "axially spaced illumination" technology, perhaps incorporating features of the "oriented cell, off-axis detector technology", may be able to accurately analyze a cell when flow orthogonal, cell cross section long axis and the intended, flow orthogonal, cell cross section long axis alignment line form an angle that is from 0 to 90 degrees (e.g., where flow orthogonal projector axes of two EMR projectors define a 45 degree angle, and two sets of detectors with mutually orthogonal axes, where one detector axis of one set is aligned with one projector axis, and one detector axis of the other set is aligned with the other projector axis). With enough projectors, as explained above, oriented properly, and with EMR detectors configured in coordination therewith, as also explained, radial orientation may become irrelevant in the analysis problem. It is of note that, regardless of the specific focus of the inventive technology, it may include a mammal birthed (born) after an insemination with a sperm cell sorted using the apparatus of, or according to the method of, any of the various embodiments of the inventive technology.

As can be easily understood from the foregoing, the basic concepts of the present invention may be embodied in a variety of ways. It involves both particle analysis techniques as well as devices to accomplish the appropriate analysis. In this application, the particle analysis techniques are disclosed as part of the results shown to be achieved by the various devices described and as steps which are inherent to utilization. They are simply the natural result of utilizing the devices as intended and described. In addition, while some devices are disclosed, it should be understood that these not only accomplish certain methods but also can be varied in a number of ways. Importantly, as to all of the foregoing, all of these facets should be understood to be encompassed by this disclosure.

The reader should be aware that the specific discussion may not explicitly describe all embodiments possible; many alternatives are implicit. It also may not fully explain the generic nature of the invention and may not explicitly show how each feature or element can actually be representative of a broader function or of a great variety of alternative or equivalent elements. Again, these are implicitly included in this disclosure. Where the invention is described in device-oriented terminology, each element of the device implicitly performs a function. Apparatus claims may not only be included for the device described, but also method or process claims may be included to address the functions the invention and each element performs. Neither the description nor the terminology is intended to limit the scope of the claims that will be included in any subsequent patent application.

It should also be understood that a variety of changes may be made without departing from the essence of the invention. Such changes are also implicitly included in the description. They still fall within the scope of this invention. A broad disclosure encompassing both the explicit embodiment(s) shown, the great variety of implicit alternative embodiments, and the broad methods or processes and the like are encompassed by this disclosure and may be relied upon when drafting the claims for any subsequent patent application. It should be understood that such language changes and broader or more detailed claiming may be accomplished at a later date (such as by any required deadline) or in the event the applicant subsequently seeks a patent filing based on this filing. With this understanding, the reader should be aware that this disclosure is to be understood to support any subsequently filed patent application that may seek examination of as broad a base of claims as deemed within the applicant's right and may be designed to yield a patent covering numerous aspects of the invention both independently and as an overall system.

Further, each of the various elements of the invention and claims may also be achieved in a variety of manners. Additionally, when used or implied, an element is to be understood as encompassing individual as well as plural structures that may or may not be physically connected. This disclosure should be understood to encompass each such variation, be it a variation of an embodiment of any apparatus embodiment, a method or process embodiment, or even merely a variation of any element of these. Particularly, it should be understood that as the disclosure relates to elements of the invention, the words for each element may be expressed by equivalent apparatus terms or method terms—even if only the function or result is the same. Such equivalent, broader, or even more generic terms should be considered to be encompassed in the description of each element or action. Such terms can be substituted where desired to make explicit the implicitly broad coverage to which this invention is entitled. As but one example, it should be understood that all actions may be expressed as a means for taking that action or as an element which causes that action. Similarly, each physical element disclosed should be understood to encompass a disclosure of the action which that physical element facilitates. Regarding this last aspect, as but one example, the disclosure of a "sorter" should be understood to encompass disclosure of the act of "sorting"—whether explicitly discussed or not—and, conversely, were there effectively disclosure of the act of "sorting", such a disclosure should be understood to encompass disclosure of a "sorter" and even a "means for sorting" Such changes and alternative terms are to be understood to be explicitly included in the description.

Any acts of law, statutes, regulations, or rules mentioned in this application for patent; or patents, publications, or other references mentioned in this application for patent are hereby incorporated by reference. Any priority case(s) claimed by this application is hereby appended and hereby incorporated by reference, as are any Exhibits. In addition, as to each term used it should be understood that unless its utilization in this application is inconsistent with a broadly supporting interpretation, common dictionary definitions should be understood as incorporated for each term and all definitions, alternative terms, and synonyms such as contained in the Random House Webster's Unabridged Dictionary, second edition are hereby incorporated by reference. Finally, all references listed in the list of References To Be Incorporated By Reference In Accordance With The Patent Application or other information statement filed with the application are hereby appended and hereby incorporated by reference, however, as to each of the above, to the extent that such information or statements incorporated by reference might be considered inconsistent with the patenting of this/these invention(s) such statements are expressly not to be considered as made by the applicant(s).

I. U.S. Patent Documents

| DOCUMENT NO. & KIND CODE (if known) | PUB'N DATE mm-dd-yyyy | PATENTEE OR APPLICANT NAME |
|---|---|---|
| 3,299,354 | Dec. 17, 1967 | Hogg |
| 3,547,526 | Dec. 15, 1970 | Devereux |
| 3,661,460 | May 09, 1972 | Elking et al. |
| 3,710,933 | Jan. 16, 1973 | Fulwyler et al. |
| 3,761,941 | Sep. 25, 1973 | Robertson |
| 3,810,010 | May 07, 1974 | Thom |
| 3,826,364 | Jul. 30, 1974 | Bonner et al. |
| 3,833,796 | Nov. 03, 1974 | Fetner et al. |
| 3,909,744 | Sep. 30, 1975 | Wisner et al. |
| 3,947,093 | Mar. 30, 1976 | Goshima et al. |
| 3,960,449 | Jul. 01, 1976 | Carleton et al. |
| 3,963,606 | Jun. 15, 1976 | Hogg |
| 3,973,196 | Aug. 03, 1976 | Hogg |
| 4,014,611 | Mar. 29, 1977 | Simpson et al. |
| 4,070,617 | Jan. 24, 1978 | Kachel et al. |
| 4,162,282 | Jul. 24, 1979 | Fulwyler et al. |
| 4,179,218 | Dec. 18, 1979 | Erdmann et al. |
| 4,200,802 | Apr. 29, 1980 | Salzman et al. |
| 4,230,558 | Oct. 28, 1980 | Fulwyler |
| 4,255,021 | Mar. 10, 1981 | Brunsden |
| 4,274,740 | Jun. 23, 1981 | Eidenschink et al. |
| 4,302,166 | Nov. 24, 1981 | Fulwyler et al. |
| 4,317,520 | Mar. 02, 1982 | Lombardo et al. |
| 4,318,480 | Mar. 09, 1982 | Lombardo et al. |
| 4,318,481 | Mar. 09, 1982 | Lombardo et al. |
| 4,318,482 | Mar. 09, 1982 | Barry et al. |
| 4,318,483 | Mar. 09, 1982 | Lombardo et al. |
| 4,325,483 | Apr. 20, 1982 | Lombardo et al. |
| 4,341,471 | Jul. 27, 1982 | Hogg et al. |
| 4,350,410 | Sep. 21, 1982 | Minott |
| 4,361,400 | Nov. 30, 1982 | Gray et al |
| 4,395,676 | Jul. 26, 1983 | Hollinger et al. |
| 4,400,764 | Aug. 23, 1983 | Kenyon |
| 4,422,761 | Dec. 27, 1983 | Frommer |
| 4,487,320 | Dec. 11, 1984 | Auer |
| 4,498,766 | Feb. 12, 1985 | Unterleitner |
| 4,515,274 | May 07, 1985 | Hollinger et al. |
| 4,523,809 | Jun. 18, 1985 | Toboada et al. |
| 4,538,733 | Nov. 03, 1985 | Hoffman |
| 4,598,408 | Jul. 01, 1986 | O'Keefe |
| 4,600,302 | Jul. 15, 1986 | Sage, Jr. |
| 4,631,483 | Dec. 23, 1986 | Proni et al. |
| 4,637,691 | Jan. 20, 1987 | Uehara et al. |
| 4,673,288 | Jun. 16, 1987 | Thomas et al. |
| 4,691,829 | Sep. 08, 1987 | Auer |
| 4,702,598 | Oct. 27, 1987 | Böhmer |
| 4,744,090 | May 10, 1988 | Freiberg |
| 4,758,729 | Jul. 19, 1988 | Monnin |
| 4,794,086 | Jan. 27, 1988 | Kasper et al. |
| 4,818,103 | Apr. 04, 1989 | Thomas et al. |
| 4,831,385 | May 16, 1989 | Archer et al. |
| 4,845,025 | Jul. 04, 1989 | Lary et al |
| 4,942,305 | Jul. 17, 1990 | Sommer |
| 4,981,580 | Jan. 01, 1991 | Auer |
| 4,983,038 | Jan. 22, 1991 | Ohki et al. |
| 5,005,981 | Apr. 09, 1991 | Schulte et al. |
| 5,007,732 | Apr. 16, 1991 | Ohki et al |
| 5,030,002 | Jul. 09, 1991 | North, Jr. |
| 5,079,959 | Jan. 14, 1992 | Miyake et al. |
| 5,098,657 | Mar. 24, 1992 | Blackford et al. |
| 5,101,978 | Apr. 07, 1992 | Marcus |
| 5,127,729 | Jul. 07, 1992 | Oetliker et al |
| 5,132,548 | Jul. 21, 1992 | Borden et al. |
| 5,144,224 | Sep. 01, 1992 | Larsen |
| 5,150,313 | Sep. 22, 1992 | Van den Engh et al. |
| 5,159,397 | Oct. 27, 1992 | Kosaka et al. |
| 5,159,403 | Oct. 27, 1992 | Kosaka |
| 5,167,926 | Dec. 01, 1992 | Kimura et al. |
| 5,180,065 | Jan. 19, 1993 | Touge et al. |
| 5,182,617 | Jan. 26, 1993 | Yoneyama et al. |
| 5,199,576 | Apr. 06, 1993 | Corio et al. |
| 5,215,376 | Jun. 01, 1993 | Schulte et al. |
| 5,247,339 | Sep. 21, 1993 | Ogino |
| 5,259,593 | Nov. 09, 1993 | Orme et al. |
| 5,260,764 | Nov. 09, 1993 | Fukuda et al. |
| 5,298,967 | Mar. 29, 1994 | Wells |
| 5,359,907 | Nov. 01, 1994 | Baker et al |

-continued

| DOCUMENT NO. & KIND CODE (if known) | PUB'N DATE mm-dd-yyyy | PATENTEE OR APPLICANT NAME |
| --- | --- | --- |
| 5,370,842 | Dec. 06, 1994 | Miyazaki et al |
| 5,412,466 | May 02, 1995 | Ogino |
| 5,452,054 | Sep. 19, 1995 | Dewa et al. |
| 5,466,572 | Nov. 14, 1995 | Sasaki, et al. |
| 5,467,189 | Nov. 14, 1995 | Kreikebaum et al. |
| 5,471,299 | Nov. 28, 1995 | Kaye et al |
| 5,483,469 | Jan. 09, 1996 | Van den Engh et al. |
| 5,558,998 | Sep. 24, 1996 | Hammond, et al. |
| 5,596,401 | Jan. 21, 1997 | Kusuzawa |
| 5,601,235 | Feb. 11, 1997 | Booker et al |
| 5,602,349 | Feb. 11, 1997 | Van den Engh |
| 5,641,457 | Jul. 24, 1997 | Vardanega, et al. |
| 5,643,796 | Jul. 01, 1997 | Van den Engh et al. |
| 5,650,847 | Jul. 22, 1997 | Maltsev et al. |
| 5,675,401 | Oct. 07, 1997 | Wangler et al. |
| 5,684,575 | Nov. 04, 1997 | Steen |
| 5,700,692 | Dec. 23, 1997 | Sweet |
| 5,707,808 | Jan. 13, 1998 | Roslaniec et al. |
| 5,708,868 | Jan. 13, 1998 | Ishikawa |
| 6,819,411 | Nov. 16, 2004 | Sharpe et al. |

II. Foreign Patent Documents

| Foreign Patent Document Country Code, Number, Kind Code (if known) | PUB'N DATE mm-dd-yyyy | PATENTEE OR APPLICANT NAME |
| --- | --- | --- |
| EP0160201A2 | Nov. 06, 1985 | Becton, Dickinson & Company |
| EP025296A2 | Mar. 18, 1981 | Ortho Diagnostic Systems Inc. |
| EP0468100A1 | Jan. 29, 1992 | TOA Medical Electronics Co., Ltd. |
| FR2699678-A1 | Dec. 23, 1992 | Union Stes Coup Agricoles |
| JP2024535 | Jan. 26, 1990 | Canon Inc. |
| JP4126064 (A) | Apr. 27, 1992 | Nitto Shokai: KK Shiomi Atsushi |
| JP4126065 (A) | Apr. 27, 1992 | Okonogi Saburo |
| JP4126066 (A) | Apr. 27, 1992 | PCC Technol: KK |
| JP4126079 (A) | Apr. 27, 1992 | Daiwa Kasei KK |
| JP4126080 (A) | Apr. 27, 1992 | Ukada Juzo Nippon Shokuhin Kako Co Ltd |
| JP4126081 (A) | Apr. 27, 1992 | PCC Technol: KK |
| JP61139747 (A) | Jun. 27, 1986 | Canon Inc. |
| JP61159135 (A) | Jul. 18, 1986 | Canon Inc. |
| SU1056008 | Nov. 23, 1983 | Stepanov Sergej, SU |
| SU1260778-A1 | Sep. 30, 1986 | TSNI Rentgeno-Radiologicheskij Institut |
| WO 98/34094 | Feb. 02, 1998 | The Horticulture and Food Research Institute of New Zealand |
| WO 2003020877 A2 | Aug. 15, 2002 | Pharmacia Corp. (c/o Monsanto Company) |

III. Non-Patent Literature Documents

Axicon; Journal of the Optical Society of America; Vol. 44, #8, Eastman Kodak Company, Hawk-Eye Works, Rochester, NY, Sep. 10, 1953, pp. 592-597
Celestron; Telescope Basics; www.celestron.com/tb-2ref.htm; 4 pages
Garner, D. L. et al; "Quantification of the X- and Y-Chromosome-Bearing Spermatozoa of Domestic Animals by Flow Cytometry[1], Biology of Reproduction 28, pgs. 312-321, (1983)
Gottlinger et al., "Operation of a Flow Cytometer", Flow Cytometry and Cell Sorting, A. Radbruch (Ed.), 1992, pp. 7-23
Johnson, Lawrence A., "Sex Preselection by Flow Cytometric Separation of X and Y Chromosome-bearing Sperm based on DNA Difference: a Review, Reprod. Fertil. Dev., 1995, 7, pgs. 893-903
Melamed et al, "An Historical Review of the Development of Flow Cytometers and Sorters", 1979, pp. 3-9
Pinkel et al., "Flow Chambers and Sample Handling,", Flow Cytometry: Instrumentation and Data Analysis, Van Dilla et al. (Eds.), 1985, pp. 77-128
Sharpe, John C. et al., "A New Optical Configuration for Flow Cytometric sorting of Aspherical Cells", Dept. of Physics and Electronic engineering, University of Waidato, Hamilton, New Zealand, November 1997, pp. 334-341.
Sharpe, Johnathan, Thesis; "An Introduction of Flow Cytometry," Chaptr. 2-2.2, 1997
Sharpe, Johnathan, Thesis; "Gender Preselection-Principle Scientific Options," Chapter. 3.4-3.4.8, 1997
Sharpe, Johnathan, Thesis; "Sperm Sexing using Flow Cytometry," Chapter. 3.5-3.5.8, 1997
Sharpe, Johnathan, Thesis; "Sperm Sexing-Method of Johnson et al," Chapter. 3.6-4.3.4, 1997
Sharpe, Johnathan, Advances in flow cytometry for sperm sexing, Unpublished paper, 2008
Skogen-Hagenson, M. J. et al; "A High Efficiency Flow Cytometer," The Journal of Histochemistry and Cytochemistry, Vol. 25, No. 7, pp. 784-789, 1977, USA
Van Dilla, Martin, "Overview of Flow Cytometry: Instrumentation and Data Analysis", Flow Cytometry: Instrumentation and Data Analysis, Van Dilla et al. (Eds.), 1985, pp. 1-8

Thus, the applicant(s) should be understood to have support to claim and make a statement of invention to at least: i) each of the analysis devices as herein disclosed and described, ii) the related methods disclosed and described, iii) similar, equivalent, and even implicit variations of each of these devices and methods, iv) those alternative designs which accomplish each of the functions shown as are disclosed and described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) each system, method, and element shown or described as now applied to any specific field or devices mentioned, x) methods and apparatuses substantially as described hereinbefore and with reference to any of the accompanying examples, xi) the various combinations and permutations of each of the elements disclosed, xii) each potentially dependent claim or concept as a dependency on each and every one of the independent claims or concepts presented, and xiii) all inventions described herein.

In addition and as to computer aspects and each aspect amenable to programming or other electronic automation, the applicant(s) should be understood to have support to claim and make a statement of invention to at least: xvi) processes performed with the aid of or on a computer as described throughout the above discussion, xv) a programmable apparatus as described throughout the above discussion, xvi) a computer readable memory encoded with data to direct a computer comprising means or elements which function as described throughout the above discussion, xvii) a computer configured as herein disclosed and described, xviii) individual or combined subroutines and programs as herein disclosed and described, xix) the related methods disclosed and described, xx) similar, equivalent, and even implicit variations of each of these systems and methods, xxi) those alternative designs which accomplish each of the functions shown as are disclosed and described, xxii) those alternative designs and methods which accomplish each of the functions shown as are implicit to accomplish that which is disclosed and described, xxiii) each feature, component, and step shown as separate and independent inventions, and xxiv) the various combinations and permutations of each of the above.

With regard to claims whether now or later presented for examination, it should be understood that for practical reasons and so as to avoid great expansion of the examination burden, the applicant may at any time present only initial claims or perhaps only initial claims with only initial dependencies. The office and any third persons interested in potential scope of this or subsequent applications should understand that broader claims may be presented at a later date in this case, in a case claiming the benefit of this case, or in any continuation in spite of any preliminary amendments, other amendments, claim language, or arguments presented, thus throughout the pendency of any case there is no intention to disclaim or surrender any potential subject matter. It should be understood that if or when broader claims are presented, such may require that any relevant prior art that may have been considered at any prior time may need to be re-visited since it is possible that to the extent any amendments, claim language, or arguments presented in this or any subsequent application are considered as made to avoid such prior art, such reasons may be eliminated by later presented claims or the like. Both the examiner and any person otherwise interested in existing or later potential coverage, or considering if there has at any time been any possibility of an indication of disclaimer or surrender of potential coverage, should be aware that no such surrender or disclaimer is ever intended or ever exists in this or any subsequent application. Limitations such as arose in Hakim v. Cannon Avent Group, PLC, 479 F.3d 1313 (Fed. Cir 2007), or the like are expressly not intended in this or any subsequent related matter. In addition, support should be understood to exist to the degree required under new matter laws—including but not limited to European Patent Convention Article 123(2) and United States Patent Law 35 USC 132 or other such laws—to permit the addition of any of the various dependencies or other elements presented under one independent claim or concept as dependencies or elements under any other independent claim or concept. In drafting any claims at any time whether in this application or in any subsequent application, it should also be understood that the applicant has intended to capture as full and broad a scope of coverage as legally available. To the extent that insubstantial substitutes are made, to the extent that the applicant did not in fact draft any claim so as to literally encompass any particular embodiment, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative embodiments.

Further, if or when used, the use of the transitional phrase "comprising" is used to maintain the "open-end" claims herein, according to traditional claim 1nterpretation. Thus, unless the context requires otherwise, it should be understood that the term "comprise" or variations such as "comprises" or "comprising", are intended to imply the inclusion of a stated element or step or group of elements or steps but not the exclusion of any other element or step or group of elements or steps. Such terms should be interpreted in their most expansive form so as to afford the applicant the broadest coverage legally permissible. The use of the phrase, "or any other claim" is used to provide support for any claim to be dependent on any other claim, such as another dependent claim, another independent claim, a previously listed claim, a subsequently listed claim, and the like. As one clarifying example, if a claim were dependent "on claim 20 or any other claim" or the like, it could be re-drafted as dependent on claim 1, claim 15, or even claim 715 (if such were to exist) if desired and still fall with the disclosure. It should be understood that this phrase also provides support for any combination of elements in the claims and even incorporates any desired proper antecedent basis for certain claim combinations such as with combinations of method, apparatus, process, and the like claims.

Finally, any claims set forth at any time are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

The following Exhibit—appearing from here to the start of the claims—relates more directly to the experiments performed in connection with the inventive technology. In interpreting the claims, it is the above text—and not the text of the Exhibit below—which controls. In the same vein, any constraining language in the Exhibit which might appear to indicate that the invention by necessity must include certain features is not to limit the claims in any fashion. Further, the references cited at the end of the Exhibit are incorporated herein.

EXHIBIT 1 -EXPERIMENTAL TEST RESULTS

Abstract (Exhibit 1)

Background: Flow cytometric sorting of X and Y chromosome-bearing sperm for gender preselection in mammals has recently progressed to industrial application. However, the accuracy, throughput, and efficiency of this technique for measuring and sorting cells is highly dependent on effective fluidic orientation of the flat sperm heads relative to the excitation source and photodetectors. Methods: In this report, a new quad-detector optical system is presented for improved efficiency and sort throughput. The design of this system has been augmented and optimised with optical studies on sperm cells through simulations (Monte Carlo model of directional fluorescence around a sperm head) and experimental results from excitation angle studies. Results: The quad-detector system provides an increase in live X sperm cells that can be accurately measured and sorted for DNA content from the current 34% to over 40% (from a mean sort rate of 6000 to over 7000 cells $s^{-1}$), at input event rates exceeding 35,000 cells $s^{-1}$. It is found that this improvement in orientation efficiency can be achieved without the need for additional laser paths or fluidic modifications over existing systems and without compromising sort purity. Conclusions: The quad-detector optical system provides a potential pathway for increased throughput rates and reduced sample waste of non-oriented cells for sperm analysis and sorting where samples are expensive or precious, such as in breeding domestic and endangered species, or in other aspherical particle measurements.

Introduction (Exhibit 1)

The spermatozoa from most mammalian species contain either an X or Y DNA chromosome pertaining to genetic information for the gender of an offspring when an egg is fertilized. By staining the DNA with a suitable fluorochrome, it is possible to differentiate X from Y sperm based on the total difference in fluorescence which ranges for different species but is approximately a 4% difference for bovine cattle. Since the first reports of sperm analysis using flow cytometry[1,2], there has been considerable interest in using the technology for sperm sexing and subsequent gender pre-selection in human and non-human mammals. Early reports on successfully sexed sperm cells[1] and the first live births with altered sex ratios[2] have spurred developments for gender balancing in humans[3], in endangered species programs[5,6], and, more recently, in cattle breeding[4]. The ramp-up to commercial use of flow cytometry as an industrial sorting tool has been made possible through improvements in sample handling pre- and post-sorting, and through modification of several aspects of flow cytometer instrumentation to improve orientation and X-Y resolution. Many mammalian sperm cells are paddle shaped with two axes of mirror symmetry[8]. Approximate dimensions for bull/bovine sperm heads are 9 $\mu$m (length)×4.5 $\mu$m (width)×1 $\mu$m (thickness) with a 40 $\mu$m tail[9,12]. This cell geometry can result in measurement errors (optical artifacts) when trying to measure the approximate 4% difference (as observed by an approximate 2:1 fluorescence ratio) which are due to the variable orientation of the cells with respect to the optical system of a traditional flow cytometer. Early studies on aspherical cells and, later, sperm cells led to a number of improvements in orienting sperm through hydrodynamic effects in the nozzle with a view to sorting[10,11]. A further modification replaced the traditional forward scatter detector of a flow cytometer with a photomultiplier tube for increased fluorescence sensitivity[11] and convenient utilization of the mirror symmetry properties of bovine sperm. Combined, these modifications have been used incorporated on a commercial instrument (MoFlo SX, Dako/Cytomation, CO) that is capable of orienting between 60% to 70% of intact live sperm cells with input analysis rates approaching 35,000 cells s$^{-1}$ and output sort rates of up to 6,000 X- and Y-sperm per second[4]. However operating these rates represent a sort efficiency of only 34% of each of the available live X or Y cells presented to the interrogation zone. Sort efficiency and therefore throughput is further limited when operating under these conditions through statistical factors and instrument processing limitations such as dead time, droplet coincidence, and overlap between X and Y populations, due to coefficient of variation for instrument and biological considerations, and the desired level of confidence required for sort regions and the desired X or Y sort purity (typically greater than 90%). The observed cell loss due to imperfect orientation is typically 30% to 40% which results in this proportion of sample passing through the instrument directly to waste since it cannot be measured accurately. This loss unnecessarily ties up instrument processing time, and for the case of high-cost, precious, or limited (i.e. frozen semen from dead animals or endangered species) sperm samples wastes this proportion of genetic material in the sample, and ultimately limits end-user benefits.

Apart from early work on studying and modifying cell orientation little research has been conducted to improve the optical detection system specifically for aspherical cells such as sperm. Efforts to overcome the optical artefacts introduced by sperm head shape have largely been directed at fluidic orientation modifications. Early epi-illumination systems provided good orientation-independent resolution[13], however their closed flow cells made high speed sorting impractical. Slit scan investigations found no preference for head- versus tail-first flow of intact sperm cells through the inspection point[14]. A radially symmetric optical system that employed a paraboloidal reflector encircling the entire jet hence utilizing a single optical collection element was reported to overcome the cell orientation dependence at low event rates[15]. An alternative approach to overcoming orientation effects investigated the use of interferometry to resolve unstained X and Y sperm heads, however this approach did not yield sufficiently low CVs to enable sufficient purity and sort speed[16].

Despite the aforementioned 30% to 40% losses due to improper cell orientation, state-of-the-art instruments still combine a single laser beam and two orthogonally (at 0° and 90° to the beam) positioned photodetectors for sperm sorting.

Here, we present a new approach to the high-resolution analysis of aspherical cells such as sperm by modelling fluorescence profiles and studying the angular dependence of illumination and detection in a flow cytometer. We introduce an augmented quad optical detection system in an effort to reclaim some proportion of cells that currently go directly to waste. With sorting in mind, this system is tested for specific ability to resolve DNA content of X and Y bearing sperm to determine the likely utility of this approach in sperm sexing and other high resolution flow cytometry measurement applications.

Materials and Methods (Exhibit 1)

Preparation of Sperm Cells for Analysis and Sorting

Aliquots of fresh bull semen were extended in a HEPES-based TALP to a final concentration of 160×10$^6$ cells ml$^{-1}$ as determined by a NucleoCounter SP-100 (ChemoMetec A/S, Allerod, Denmark). A Hoechst 33342 (HO, Invitrogen Corp., Eugene, Oreg.) staining TALP (Bis-Benzimide, H-33342; H21492, Molecular Probes) was added to this sample and incubated over a 45 minute period at 34.5° C. (final HO stain concentration 72.9 $\mu$M or 9 $\mu$l ml$^{-1}$). After sample incubation, an equivalent volume of buffer was added to adjust the pH of the solution from approximately 7.4 to 6.8 to optimise sperm health to produce a final sample concentration of 80×10$^6$ cells ml$^{-1}$. This buffer also contained a food colouring agent (Red #40, Warner Jenkinson Co., Inc, St. Louis, Mo.) that acts to quench HO fluorescence from dead cells in order to provide a means for specifically sorting live cells. Samples were pipetted from this mixture into 5 ml polypropelene test tubes for analysis and sorting on the flow cytometer.

Flow Cytometry Instrumentation

A MoFlo SX sperm sorter configured for sperm sexing (Cytomation Inc., Fort Collins, Colo. recently acquired by Beckman Coulter, Fullerton, Calif.), was used for experimentation. Specific modifications for this instrument include 1) replacing the forward scatter photodiode with a 20× 0.42 numerical aperture (NA) microscope objective (Mitutoyo America Corp., Aurora, Ill.) and photomultiplier tube (PMT) to enable 0° versus 90° fluorescence (FIG. 21A), 2) using a custom-designed orienting nozzle, 3) expanding the PMT voltage range to lower values, 4) extending digital signal processing functionality for data analysis and viewing, and 5) utilizing a quasi-CW (80 MHz repetition rate) frequency-tripled Nd:YVO4 laser (Vanguard 350 mW, Newport Corporation, CA) for 355 nm excitation of the sample with a laser beam shaper that produces a 25×160 $\mu$m 1/e$^2$ spot waist at the interrogation point, and at a nominal operating output of 175 mW.

Figure 21:
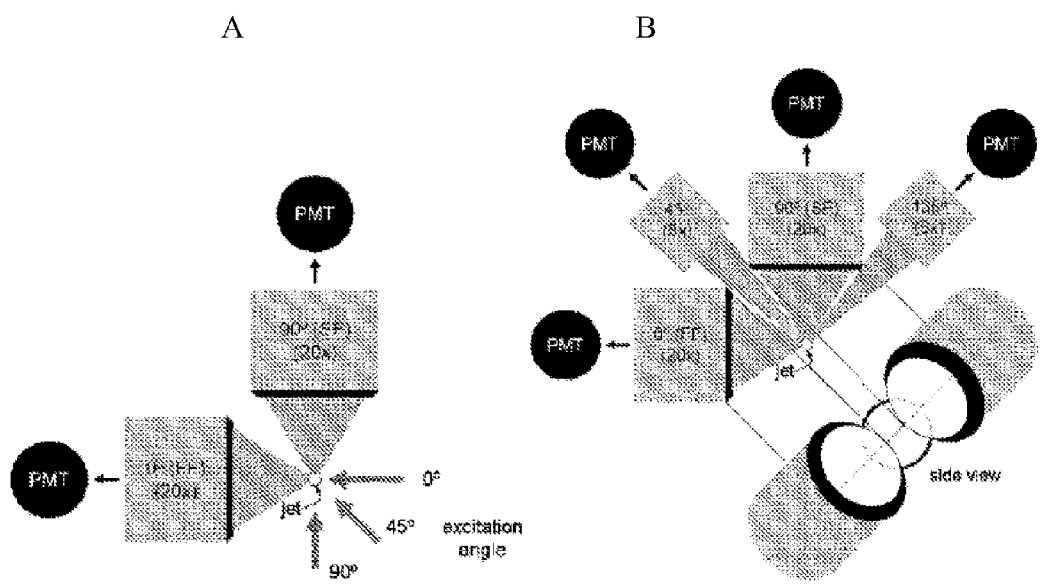
FIG. 21 A: shows a schematic (top view) of standard orthogonal detection layout for sperm DNA content analysis 0° and 90°, but with additional excitation angles of 45° and 90° over the typical 0° only B: shows quad detector layout (top and side view) showing 0°, 45°, 90° and 135° objectives, filters and PMT detectors encircling the jet in a nested configuration.

For our studies, the configuration outlined above was further modified. For excitation angle studies the laser beam was split into multiple paths as shown in FIG. 21A (with a subsequent halving of laser power in each path) to provide selective angular illumination of 0°, 45°, or 90° with respect to the standard 0° configuration. The quad-detector optical system (QDOS) is shown in top and side view projections in FIG. 21B. Here, two additional 10× objectives (NA=0.28, Mitutoyo America Corp., Aurora, Ill.) and PMTs (H957-12 Hamamatsu Corporation, Bridgewater, N.J.) are nested behind the 0° and 90° detectors at 45° and 135° from the standard 0° illumination axis to catch spill-over fluorescence outside the acceptance cone of each respective 20× objective in a master-slave arrangement. An ELP410 optical longpass filter (10LWF-400-B/51280, Newport Corp., Irvine, Calif.) was located directly in front of each detector to provide transmission of stained cell fluorescence whilst blocking laser scatter. The introduction of additional detector elements required machining modifications to be made to several of the aluminium plates that make up the MoFlo inspection tower. This nested QDOS configuration provides a horizontal band of near-continuous light collection from cells travelling through the jet centred from 0° to 135°. Thus, given the two axes of mirror symmetry, a sperm cell travelling with its longest axis parallel to that of the flow will be measurable independent of its rotational orientation about that axis. In all studies, sheath pressure was set to 2.76 bar (40 psi). Sample to sheath differential pressure was altered to obtain event rates over the range 2,000 to 50,000 events s$^{-1}$ depending on test purpose (e.g. orientation effect of nozzle or CV and split resolution studies). Unless otherwise stated, data presented in this report was obtained at 35,000 events s$^{-1}$.

Cell Fluorescence Model

A Monte Carlo ray trace simulation was devised to generate and approximate likely fluorescence emission profiles from a sperm cell. The sperm cell was modelled in Matlab (The Mathworks, Natick, Mass.) as a lens-like element and optical phenomena such as reflection, refraction, transmission, absorption, and total internal reflection were taken into account. It was assumed that the fluorochromes (light point sources) are distributed randomly throughout the sperm head. In this model, for one million randomly located start points (fluorescent molecules photon sources) several simple geometries including rectangle, capped rectangle, and elliptical were used to determine the approximate fluorescence profile for cells aligned with the longest axis along the direction of flow. Refractive index of the live sperm cell was taken as $n_c$=1.42 from a previous report[9] and the surrounding sheath fluid $n_s$=1.333. Refractive effects at the sheath fluid to air boundary were neglected since it is assumed that the cell is centered within the narrow core region of the 100□m cylindrical jet.

Results (Exhibit 1)

Cell Fluorescence Model

Figure 22:
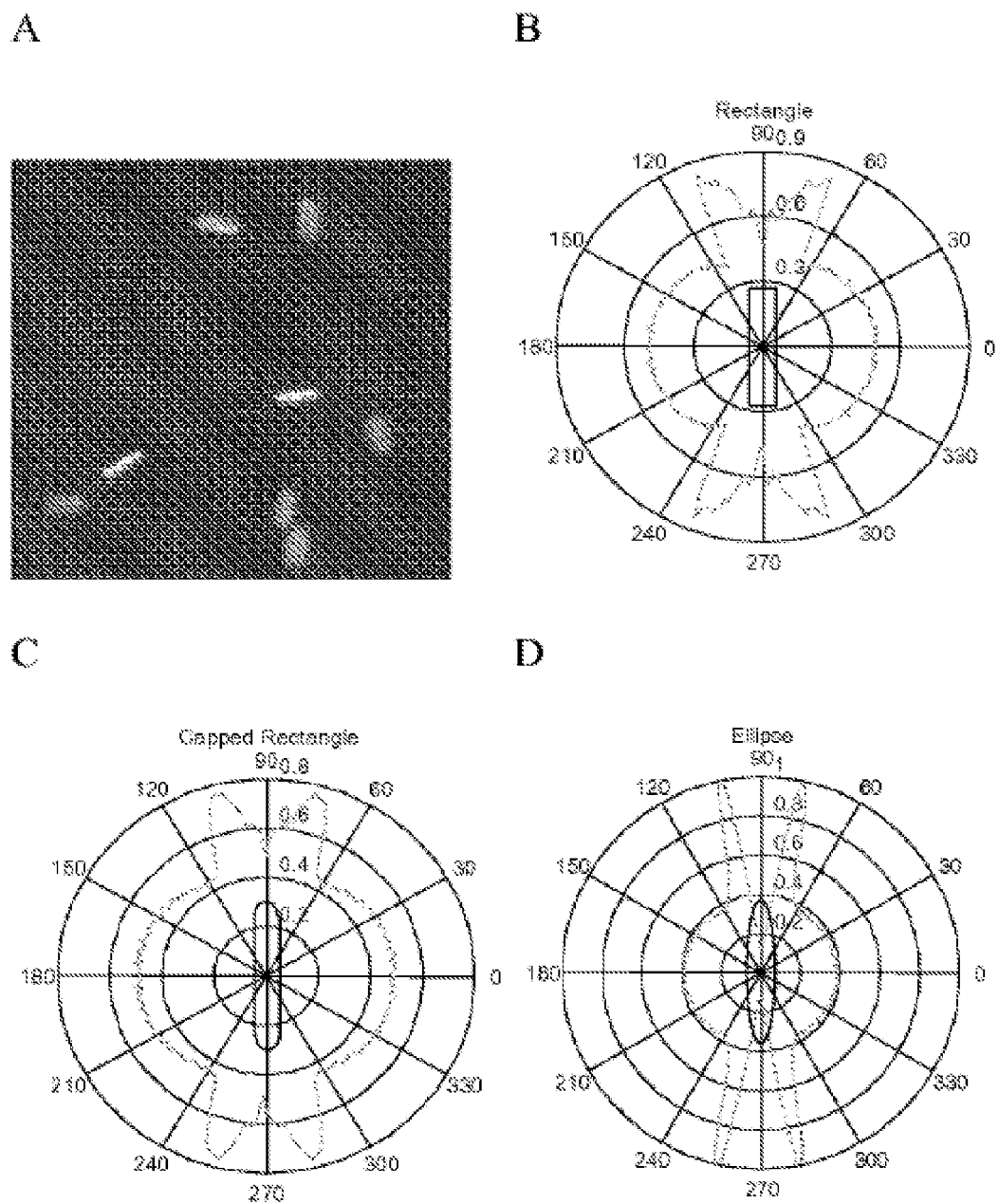
FIG. 22 A: shows an image of Hoescht 33342 stained bovine sperm obtained on a fluorescence microscope showing cells oriented edge and flat face toward observer. Monte Carlo optical (ray trace) simulation results for fluorescence intensity of a sperm cell (flow axis into page) for several geometries including B: rectangle, C: capped rectangle, and D: elliptical geometries the planes of which are perpendicular to the flow axis.

As shown in the photograph of FIG. 22A, sperm cells that are positioned edge-toward the microscope objective are brighter than those presented with their flat face showing. (The integrated signal from each of the cells is measured (using image processing software ImageJ, National Institute of Mental Health, Bethesda, Md., USA) to be approximately the same total intensity. This difference (ratio) is similar to that experienced in a flow cytometer[1,2]. However, there is very little published data, apart from an early report[2] about the approximate range of angles over which this asymmetric fluorescence profile occurs.

Our Monte Carlo model findings (FIG. 22B-D) generally support this two-fold face to edge difference in fluorescence intensity (approximately 1.6 to 1 for the capped rectangle, and 2.5 to 1 for the ellipse). The model also provides an estimate of the angular dependence of this effect, which can be used to guide the design of an appropriate optical detection geometry to provide improved resolution for aspherical cells such as the sperm cells presented here.

A dip in the intensity profile is predicted for all geometries studied. It is difficult to measure the presence or otherwise of this dip experimentally since a very low collection angle would be required, and very precise sperm cell orientation would be needed to make measurements with the necessary angular resolution, however it would be interesting to study this predicted phenomenon in more detail with appropriate (optical) instrumentation. Also of interest is the fluorescence emission ratio from the edge to face, where the model yields a peak value of between 1.6:1 for the rectangle to approximately 2.5:1 for the elliptical geometry. These values compare to a measured ratio of approximately 2:1 in our studies and those of others[2].

This result is perhaps unsurprising, since this more 'organic' elliptical profile might be expected to match the biological geometry of a cell. However when comparing our model results with experimental values one must also consider the solid angle or acceptable angle of optical elements used for light collection which will integrate and therefore dampen the observation of angle dependence on measured fluorescence. Irrespective of the geometry modelled, a near-uniform fluorescence intensity profile is predicted over an angular range of ±60° out the flat face of the sperm cell. This observation is important when selecting optical elements for sperm fluorescence measurement. This is to ensure that a sufficient number of light collection elements are employed when low NA elements are used, or that measurement errors are not introduced where high NA elements are used (i.e. with collection angles greater than ±60° that would integrate light emitted from the flat face and narrow edge of sperm cells therefore lessening measurement precision).

Cell Orientation vs. Measured Fluorescence

Figure 23:
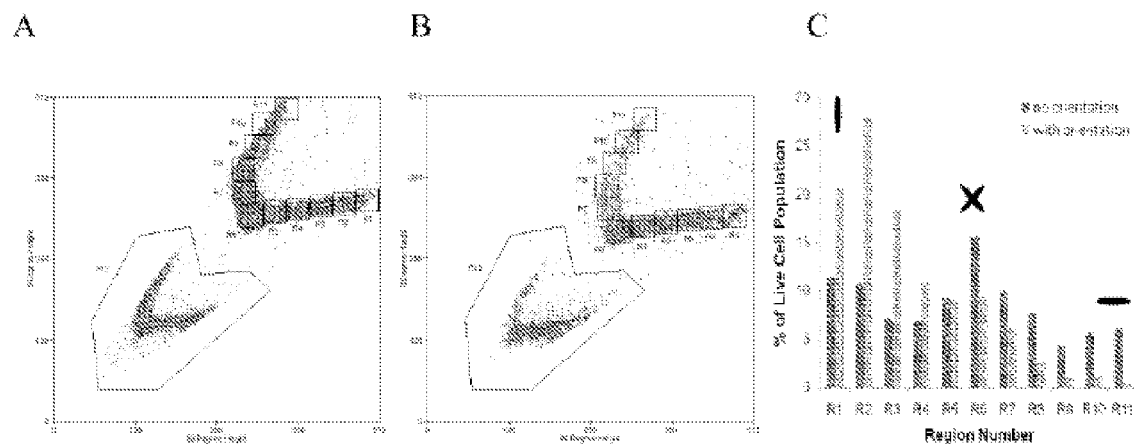
FIG. 23 shows the effect of fluidic orientation on sperm cells through the inspection point of a flow cytometer. A: no orientation B: Orientation C: percentage of cells falling within each of 11 regions of equivalent size across live sperm population without and with fluidic orientation at an event rate of 35,000 eps.

FIG. 23 shows bivariate 0° vs. 90° Hoechst 33342 fluorescence intensity plots for live stained sperm cells excited in a traditional 0° beam excitation geometry with (FIG. 23A) and without (FIG. 23B) planar fluidic cell orientation at an event rate of 25,000 events s$^{-1}$. Both plots exhibit a characteristic L-shaped population representing cells that are edge-toward the 90° detector (lower right), edge toward the 0° detector (upper left), or oriented somewhere in between. Dead and transitional cells can be seen in the lower left region (region R12) of the plot in a lower intensity profile that mimics that of the live cells. It has been observed that intact sperm cells tend to be aligned with their longest axis along that of their direction of flow[14]. In this arrangement, cells that are oriented edge-toward the 90 detector are typically gated somewhat arbitrarily and analysed for commercial high resolution X-Y DNA measurement and sorting. In FIG. 22C the percentage of the total live cell population contained within sub-populations falling into each of a number (11) of similar-sized regions from the lower right (R1) to the upper left (R11) of the L population is shown which represents approximately 0° to 90° cell orientation. From this graph, the effect of fluidic orientation can clearly be seen by a curve shifted toward the left indicating an increase in the proportion of cells aligned with respect to the side detector. In regions 1-4 (equivalent to the region that an orientation gate would be set for sorting), approximately 70% of the live population is oriented vs. 25% without fluidic orientation. R6 has an artificially high percentage (approximately twice the number) of cells for both data sets since at this angle with an orthogonal detector arrangement it is not possible to distinguish cells oriented at 45° to the excitation source from those oriented exactly 90° away at 135°. From this data set it can be seen that with fluidic orientation employed approximately 5% of cells remain immeasurable because they do not produce clear XY differences. Possible reasons for this include 1) cells not being at an appropriate angle to the detectors to enable reliable high-resolution measurement out the flat face, and 2) cells oriented near edge-on to the excitation source that present a smaller cross-sectional area for efficient light capture and therefore fluorescence.

Excitation Angle vs. Fluorescence

Figure 24:
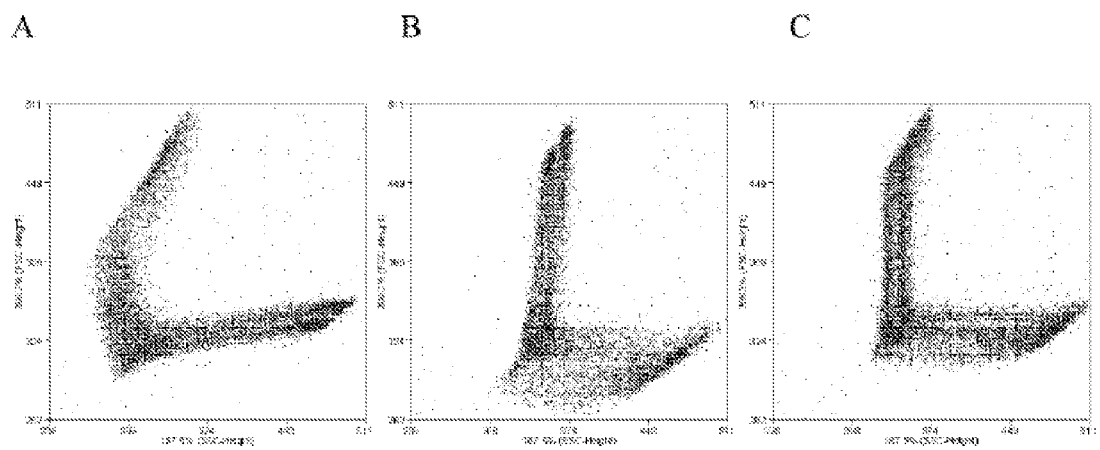
FIG. 24 shows the effect of illumination angle on 0° vs 90° sperm fluorescence profile with A: traditional 0° excitation, B: 90' excitation, and C: combined 0°+90' excitation. A zoom function has been used to view differences between data sets more clearly.

The plots presented in FIGS. 24 A-C show the effect of illumination angle (0°, 90°, and 0°+90° respectively) on bivariate profile for randomly oriented cells. Here the influence of illumination angle can clearly be seen. 0° Illumination (FIG. 24A) produces the characteristic L-shape with a kink part-way along the upper arm and evidence of distinct X and Y populations in the lower right region. As expected, 90° illumination (FIG. 24B) reverses the position of the kink to the lower arm, and indeed the ability to resolve X and Y sperm (the role of each of the detectors has been swapped) in the upper left region. By switching both lasers on (FIG. 24C), and reducing the laser power by half to ensure constant light exposure of cells, a symmetric L shaped population is generated with evidence of splits along each arm of the L, but with curvature now appearing at each end. We can explain this result by considering that cells that are edge on to one of the lasers will absorb more light due to waveguiding than those at a slight angle and which will be more inclined to reflect light. This artefact can be overcome by spatially separating the excitation beams along the flow axis (data not shown), however commercial implications may limit the practicality of this approach since laser power would need to be doubled to ensure optimal cell excitation (which in turn increases total irradiation and dose of cells when traversing the interrogation region), and additional detectors would be required to avoid analysis rate restrictions due to particle coincidence.

Addition of 45° and 135° Detector Pair

In an attempt to increase the sort efficiency of sperm sexing, an orthogonally matched detector pair was introduced to measure cells with their edges oriented near 45° and 135° to the optical axis of the flow cytometer (FIG. 21B). This detector pair was inserted to collect spill-over light from the existing collection objectives to determine additive sort rate effects. This arrangement was also chosen after considering our cell fluorescence simulation results, illumination studies, and space constraints in and around the inspection region. This nested detection system has a number of potential advantages. First, the high first-order analysis that routinely yields greater than 60% orientation is maintained to ensure the existing measurement and sort performance is not compromised. Second, by placing optics (of a lower numerical aperture) behind the original objectives in a staggered configuration (FIG. 21B) we are able to collect light in a near-continuous band around the inspection point. Third, potential mechanical interference between expensive and or highly customised components are avoided.

Figure 25:
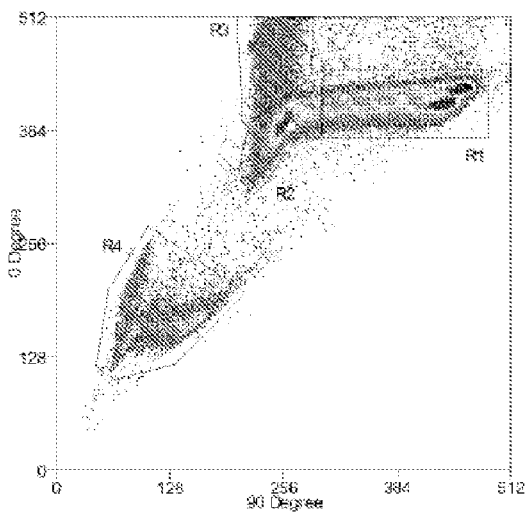
FIG. 25 shows a iuad detector fluorescence analysis of 200000 sperm cells showing A: traditional 0° vs 90° fluorescence layout with increased orientation with respect to 90° detector (R1), 0° (R3), in between (R2), and dead cells (R4), B: 45° vs 135° detector layout of all cells, C: cells gated from R2pertaining to those oriented edge-toward 45° (R5) and 135° (R6) detectors respectively, and D: bivariate showing position of R1 oriented cells as observed using 45°135° detector pair.
Figure 25:
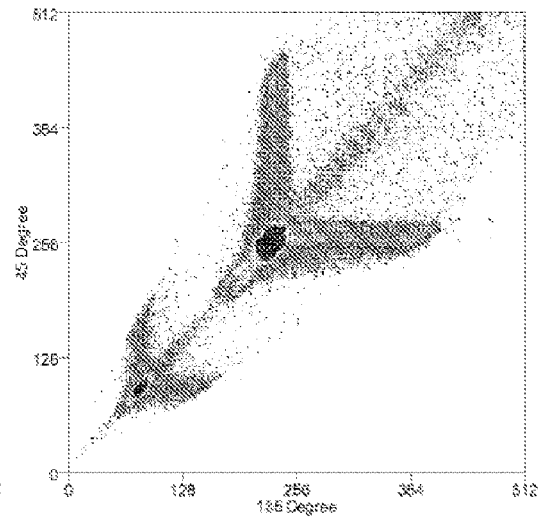
Figure 25:
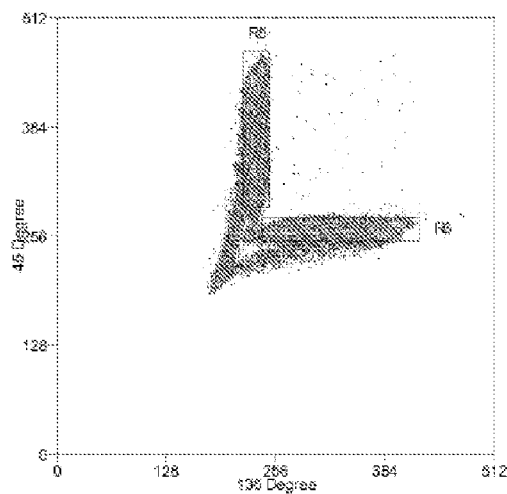
Figure 25:
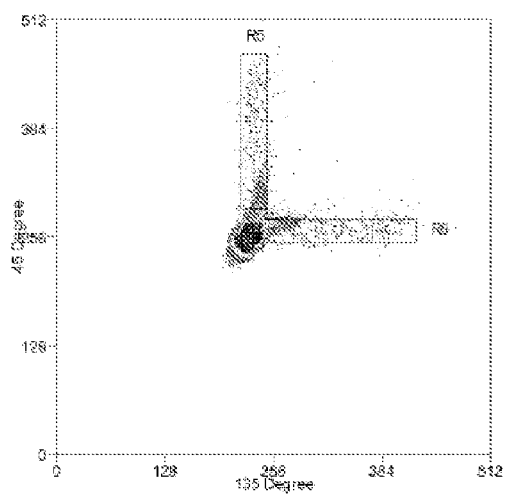

Data acquired using the quad configuration is presented in FIG. 25. It should be noted that the orienting nozzle was retained in this study to maximize cell orientation with respect to the 0°-90° and newly introduced 45°-135° detector pairs. FIG. 25A shows 0° vs. 90° Hoechst fluorescence for a typical stained sperm population with live (R1-R3) and dead (R4, 12.2% of all cells) cell populations resolved, and regions R1 (53.9%, or 61.8% of live cells), and R2 (22.4%) and R3 (7.0%) combined surrounding oriented and non-oriented cells with respect to (i.e. bright edge toward) the 90° detector. FIG. 25B shows all cells as measured by the 45°-135° detector pair. Here, the data shows a symmetric L-shape with upper left cells being oriented edge-toward 45° and lower right being oriented edge-toward 135°. This symmetry is expected since cells are exposed to similar excitation due to cross-sectional area presented to the laser for either orientation. Further insight into cell orientation can be gained by studying the gated live fractions of non-oriented cells (from R2) in FIG. 25C, and oriented cells (from R1) in FIG. 25D. Of the 22.4% from region R2, the positions shown for regions R5 and R6 amount to an additional 8.2%+9.8% (18%) available for sorting over and above the 53.9% deemed appropriate for sorting from region R1. However, in practice we find split resolution to be poorer for the 45° and 135° detectors than that for the 0° detector. We expect this difference to be due sub-optimal excitation of cells since they are at an angle to the excitation source compared to those cells in R1, and because of the significantly lower collection efficiency of the light collection optics. The exaggerated effect of sub-optimal illumination (i.e. for cells oriented edge-toward the excitation source) can be seen in FIG. 25B in populations that extent toward the lower left most part of the plot. For most live samples operating at event rates of 35,000 cells $s^{-1}$ this population represents the typical remaining 4-8% of live cells for which XY splits cannot easily be resolved.

Figure 26:
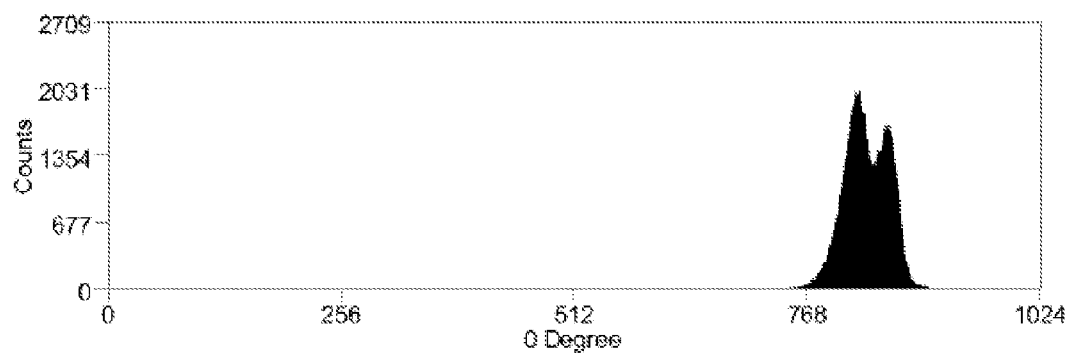
FIG. 26 shows a fluorescence histograms for sample acquired in FIG. 25 showing an XY split in each of A: 0°, B: 45°, and C: 135° detectors.
Figure 26:
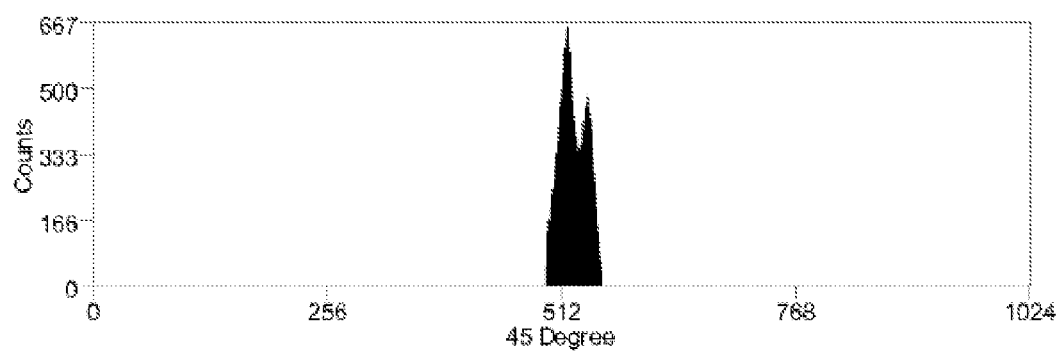
Figure 26:
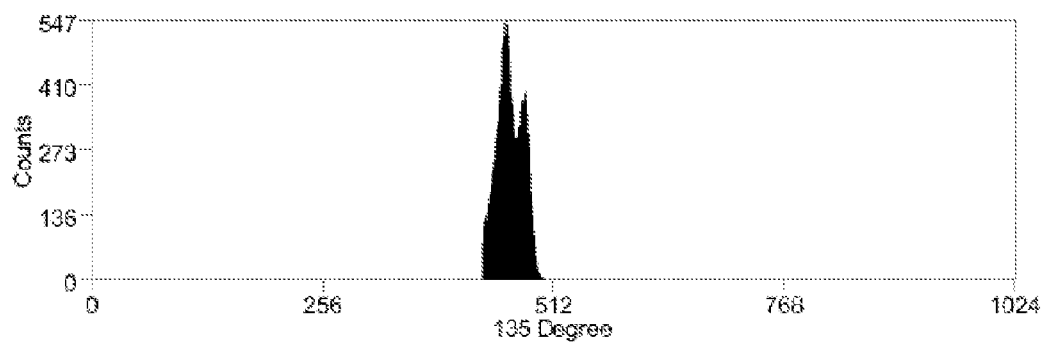

FIG. 26 shows gated histogram data for each of the high resolution detectors 0° (FIG. 26A), 45° (FIG. 26B), and 135° (FIG. 26C) from the data set provided in FIG. 25 where in each case, XY splits (4% difference) can be observed indicating that sorting high purity fractions would be possible from this sample using this detection scheme.

Importantly, the addition of 45° and 135° detectors shows that X-Y DNA measurements can be made for an additional 15-20% of live cells, and that with appropriate gating schemes, these cells could be sorted in an additive fashion to those traditionally considered to be oriented. In preliminary sorting investigations (input event rate of 35,000 cells $s^{-1}$) we have found that, depending on sample and bull ejaculate quality, it is possible to sort an additional 800 to 1500 X sperm cells $s^{-1}$ on top of approximately 4500 to 6000 cells $s^{-1}$ with no detectable difference in purity between sorted populations. Additional sorting considerations and the effect of altering event rates will be the study of further investigations, and the physiology and reproductive performance of various oriented fractions will also be considered. However, the gains from this preliminary work represent an increase in sort rates and therefore throughput of between 18-25%, with sort efficiency gains of approximately 6% of total live X sperm (i.e. from 34% to 40% of available live X cells assuming a 50:50 ratio of X:Y cells) over current commercial sperm sorting methods.

45° Illumination

Figure 27:
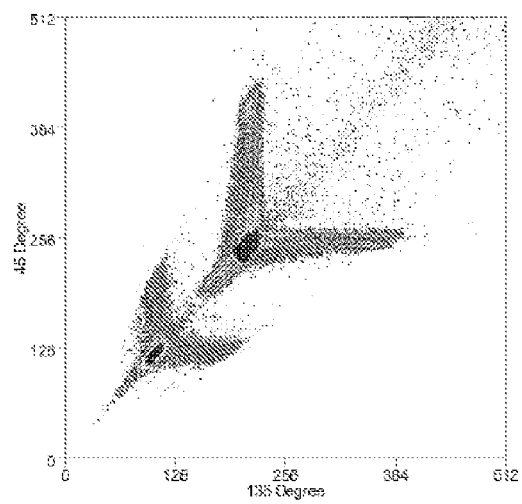
FIG. 27 shows cell illumination at A) 0°, and B) 45° with respect to 45° and 135° detector pair 5 showing orientation dependence on optimal cell excitation and DNA content measurement.
Figure 27:
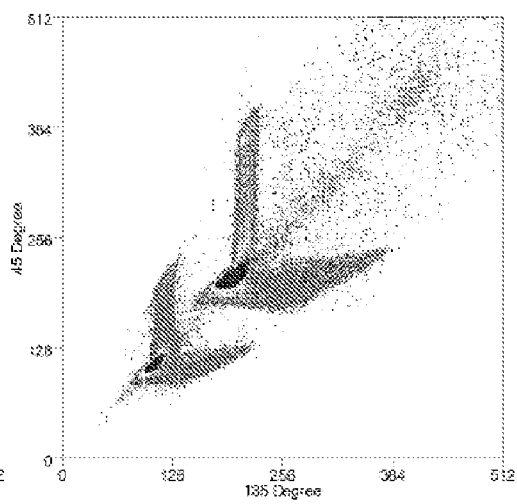

To investigate the effect of illumination angle on high resolution DNA content measurement, cells were excited at two discrete angles (0° and 45°, FIG. 21A) whilst observing 45° vs 135° fluorescence bivariate data profiles. With 0° illumination (FIG. 27A) a symmetric population is observed which shows no bias in fluorescence intensity for cells that are aligned with an edge toward either detector. However, when the excitation angle is altered to being at 45° a subtle but clearly observable skew arises. The upper left region of the live population in this plot no longer shows a shoulder to lower fluorescence intensity values with respect to the 135° detector (in fact, this plot now closely mimics that obtained with 0° illumination and 0° vs. 90° detection as expected). Thus, form this result, we can see that, for cells that are oriented at an angle of greater than approximately 45° from the preferred orientation that presents a maximal area to the excitation source, suboptimal illumination, and therefore X-Y resolution compromised. Thus, some additional means of excitation would be required if high resolution measurements are desired for cells that are greater than 45° to the preferred orientation.

Discussion (Exhibit 1)

In this report we present our findings from several studies on illumination and detection effects on cell fluorescence with sperm sexing applications in mind. By developing and using a Monte Carlo model, we have simulated the fluorescence profile around a sperm cell. Based on the data from this work combined with our illumination studies, we have designed, built and tested a quad detection system that when combined with cell orientation increases the usable fraction of cells for analysis and ultimately sorting from approximately 34% to 40% of available live X cells. Depending on the bull ejaculate used, this gain represents an additional 800 to 1500 cells that would otherwise have been sent down the waste stream per second (in addition to between 4500 to 6000 cells s$^{-1}$) that can be sorted without compromising purity. If employed into routine use, such improvements would provide advantages for commercial and scientific sperm sexing applications ranging from domestic animals to endangered species.

REFERENCES/LITERATURE CITED

1. Gledhill B L, Lake S, Steinmetz L L, Gray J W, Crawford J R, Dean P N and Van Dilla M A. Flow microfluorometric analysis of sperm DNA content: effect of cell shape on the fluorescence distribution. J Cell Physiol 1976;87:367-376.
2. Van Dilla M A, Gledhill B L, Lake S, Dean P N, Gray J W, Kachel V, Barlogie B, Gohde W. Measurement of mammalian sperm deoxyribonucleic acid by flow cytometry: problems and approaches. J Histochem Cytochem 1977;25:763-773.
3. Fugger E F. Clinical experience with flow cytometric separation of human X- and Y-chromosome bearing sperm. Theriogenology 1999;52:1345-1440.
4. Garner D L, Seidel G E. History of commercializing sexed semen for cattle. Theriogenology 2008;69:886-895.
5. O'Brien J K, Robeck T R. Development of sperm sexing and associated assisted reproductive technology for sex preselection of captive bottlenose dolphins (*Turisops trancatus*). Reprod Fertil Dev 2006;18:319-219.
6. O'Brien J K, Stojanov T, Chriton E G, Evans K M, Evans G, Maxwell W M C. Flow cytometric sorting of fresh and frozen-thawed spermatozoa in the lowland gorilla (*Gorilla gorilla gorilla*). Am J Primatl 2005;66:297-315.
7. Johnson L A, Flook J P, Look M V, Pinkel D. Flow Sorting of X and Y chromosome-bearing spermatozoa into two populations. Gamete Research 1987;16:1-9.
8. Johnson L A, Flook J P, Hawk H W. Sex preselection in rabbits: live births from X and Y sperm separated by DNA and cell sorting. Biology of Reproduction 1989;41:199-203.
9. Van Duijn C, Van Voorst C: Precision measurements of dimensions, refractive index and mass of bull spermatozoa in the living state. Mikroskopie 1971;27:142-167.
10. Kachel V, Kordwig E, Glossner E. Uniform lateral orientation, caused by flow forces, of flat particles in flow-through systems. J Histochem Cytochem 1977;25:774-780.
11. Johnson L A, D Pinkel: Modification of a laser-based flow cytometer for high resolution DNA analysis of mammalian spermatozoa. Cytometry 1986;7:268-273.
12. Garner D L. Flow cytometric sexing of mammalian sperm. Theriogenology 2006;65:943-957.
13. Skogen-Hagenson M J, Salzman G C, Mullaney P F, Brockman W H: A High Efficiency Flow Cytometer. J Histochem Cytochem 1977;25:784-789.
14. Rens W, Welch G R, Houck D W, van Oven C H, Johnson L A: Slit-scan flow cytometry for consistent high resolution DNA analysis of X- and Y-chromosome bearing sperm. Cytometry 1996;25:191-199.
15. Sharpe J S, Schaare P N, Kunnemeyer R. Radially symmetric excitation and collection optics for flow cytometric sorting of assymetrical cells. Cytometry 1997;29:363-370.
16. Van Munster E B. Interferometry in flow to sort unstained X- and Y-chromosome-bearing bull spermatozoa. Cytometry 2002;47:192-199.

Morrell J M, Keeler K D, Noakes D E, Mackenzie N M, Dresser D W: Sexing of sperm by flow cytometry. The Veterinary Record 1988;2:322-324.

We claim:

1. A cell analysis apparatus comprising:
   a cell source that includes a plurality of cells to be analyzed, each cell defining a cell long axis;
   a channel that defines a flow axis and through which said cells flow; wherein said cells, when said cell long axis is parallel with said flow axis, have at least a portion that has a flow orthogonal, cell cross-section that is non-circular, wherein said flow orthogonal, cell cross-section has a flow orthogonal, cell cross- section long axis and a flow orthogonal, cell cross-section short axis that is orthogonal to said flow orthogonal, cell cross-section long axis, wherein said channel defines an intended, flow orthogonal, cell cross section long axis alignment line and an intended, flow orthogonal, cell cross section short axis alignment line that is orthogonal to said intended, flow orthogonal, cell cross section long axis alignment line, wherein said channel is configured to orient said cells so that said cell presents at full orientation during a cell illumination, wherein, when said cell is in said full orientation:
   (a) said cell long axis is parallel with said flow axis,
   (b) said flow orthogonal, cell cross-section long axis is aligned with said intended flow orthogonal, cell cross section long axis alignment line; and
   (c) said flow orthogonal, cell cross-section short axis is aligned with said intended, flow orthogonal, cell cross section short axis alignment line;
   an EMR projector established to effect said cell illumination by projecting EMR at said cells;
   a first EMR detector and a second EMR detector, each established to detect EMR emitted as a result of said cell illumination, wherein said first EMR detector has a first detector, flow orthogonal collection angle that defines a flow orthogonal, first detector axis and said second EMR detector has a second detector, flow orthogonal collection angle that defines a flow orthogonal, second detector axis; wherein said flow orthogonal, first detector axis is substantially coaxial with said intended, flow orthogonal, cell cross section long axis alignment line, wherein said flow orthogonal, second detector axis is substantially coaxial with said intended, flow orthogonal, cell cross section short axis alignment line, wherein said flow orthogonal, first detector axis and said flow orthogonal, second detector axis are substantially 90 degrees apart; and
   a third EMR detector and a fourth EMR detector, each established to detect EMR emitted as a result of said cell illumination, wherein said third EMR detector has a third detector, flow orthogonal collection angle that defines a flow orthogonal, third detector axis and said fourth EMR detector has a fourth detector, flow orthogonal collection angle that defines a flow orthogonal, fourth detector axis, wherein said flow orthogonal, third detector axis and said flow orthogonal, fourth detector axis are substantially 90 degrees apart, and wherein said flow orthogonal, third detector axis is from 30 degrees to 60 degrees from said intended, flow orthogonal, cell cross section long axis alignment line.

2. The cell analysis apparatus of claim 1 wherein each said third and said fourth EMR detector collect EMR traveling in a flow orthogonal plane.

3. The cell analysis apparatus of 1 wherein each said third and said fourth EMR detector do not collect any EMR traveling in a direction orthogonal to the flow.

4. The cell analysis apparatus of 1 wherein said intended, flow orthogonal, cell cross section long axis alignment line defines a first side on which is established said EMR projector and a second side.

5. The cell analysis apparatus 4 wherein said flow orthogonal, second detector axis is on said second side.

6. The cell analysis apparatus as of 4 wherein said flow orthogonal, third detector axis is on said second side.

7. The cell analysis apparatus of 4 wherein said third EMR detector detects to provide information relative to said cell orientation or information relative to an intrinsic cell characteristic.

8. The cell analysis apparatus of 1 further comprises a cell sorter established down flow of a site of said cell illumination.

9. The cell analysis apparatus of 1 wherein said channel is selected from the group consisting of: an orienting nozzle tip and a microfluidic channel.

10. The cell analysis apparatus of claim 1 further comprises a motorized control that controllably adjusts the position of at least one of said detectors and said EMR projector.

11. The cell analysis apparatus of claim 1 wherein said EMR projector comprises an EMR source.

12. The cell analysis apparatus of claim 11 wherein said EMR source comprises an EMR source selected from the group consisting of a laser, an arc lamp and a LED.

13. The cell analysis apparatus of claim 1 wherein said cell illumination occurs after said cell has exited said channel.

14. The cell analysis apparatus of claim 13 wherein said cell analysis apparatus comprises a jet-in-air flow cytometer.

15. The cell analysis apparatus of claim 1 wherein each said first and said second EMR detector collect EMR traveling in a flow orthogonal plane.

16. The cell analysis apparatus of claim 1 wherein said first EMR detector detects to provide information relative to said cell orientation.

17. The cell analysis apparatus of claim 1 wherein said second EMR detector detects to provide information relative to an intrinsic cell characteristic.

18. The cell analysis apparatus of claim 17 wherein said cells to be analyzed comprise sperm cells.

19. The cell analysis apparatus of claim 18 wherein said intrinsic cell characteristic comprise X or Y chromosome.

20. The cell analysis apparatus of claim 1 further comprising an electronic data analysis system to which readings from said EMR detectors are input.

21. The cell analysis apparatus of claim 20 wherein said electronic data analysis system comprises a digital data analysis system.

22. The cell analysis apparatus of claim 1 further comprising a sheath fluid reservoir.

23. A cell analysis apparatus as described in claim 1 wherein said an EMR projector is established to effect said cell illumination by projecting EMR at said cells and in a direction substantially parallel said intended, flow orthogonal, cell cross section short axis alignment line.

* * * * *

UNITED STATES PATENT AND TRADEMARK OFFICE
CERTIFICATE OF CORRECTION

PATENT NO.      : 8,603,396 B2
APPLICATION NO. : 13/058574
DATED           : December 10, 2013
INVENTOR(S)     : Johnathan Sharpe and Kenneth Michael Evans Page 1 of 1

It is certified that error appears in the above-identified patent and that said Letters Patent is hereby corrected as shown below:

In the Claims,

Claim 3, column 31, line 14, "The cell analysis apparatus of 1" should read --The cell analysis apparatus of claim 1--

Claim 4, column 31, line 17, "The cell analysis apparatus of 1" should read --The cell analysis apparatus of claim 1--

Claim 5, column 31, line 21, "The cell analysis apparatus 4" should read --The cell analysis apparatus of claim 4--

Claim 6, column 31, line 23, "The cell analysis apparatus as of 4" should read --The cell analysis apparatus of claim 4--

Claim 7, column 31, line 25, "The cell analysis apparatus of 4" should read --The cell analysis apparatus of claim 4--

Claim 8, column 31, line 29, "The cell analysis apparatus of 1" should read --The cell analysis apparatus of claim 1--

Claim 9, column 31, line 31, "The cell analysis apparatus of 1" should read --The cell analysis apparatus of claim 1--

Signed and Sealed this
Thirtieth Day of December, 2014

Michelle K. Lee
*Deputy Director of the United States Patent and Trademark Office*